United States Patent
Kozaki et al.

(10) Patent No.: US 7,358,070 B2
(45) Date of Patent: Apr. 15, 2008

(54) PROCESS FOR FORMATION OF PATTERN OF POLYHYDROXYALKANOATE

(75) Inventors: Shinya Kozaki, Tokyo (JP); Tsutomu Honma, Atsugi (JP); Tetsuya Yano, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 235 days.

(21) Appl. No.: 11/062,816

(22) Filed: Feb. 23, 2005

(65) Prior Publication Data

US 2005/0196521 A1 Sep. 8, 2005

(30) Foreign Application Priority Data

Feb. 24, 2004 (JP) ............................. 2004-047941

(51) Int. Cl.
*C12P 7/62* (2006.01)
*A61L 2/00* (2006.01)

(52) U.S. Cl. .................. 435/135; 427/2.24; 435/252.8
(58) Field of Classification Search ................ 435/135, 435/252.8; 427/2.24
See application file for complete search history.

(56) References Cited

U.S. PATENT DOCUMENTS

| | | | |
|---|---|---|---|
| 6,476,215 B1 | 11/2002 | Okamoto et al. | 536/25.3 |
| 6,916,861 B2 * | 7/2005 | Nomoto et al. | 523/160 |
| 6,951,745 B2 * | 10/2005 | Nomoto et al. | 435/118 |
| 2002/0146715 A1 | 10/2002 | Okamoto et al. | 435/6 |
| 2003/0059817 A1 | 3/2003 | Okamoto et al. | 435/6 |
| 2003/0096115 A1 | 5/2003 | Kozaki et al. | 428/404 |
| 2003/0104302 A1 | 6/2003 | Honma et al. | 430/110.2 |
| 2003/0118931 A1 | 6/2003 | Yano et al. | 430/108.22 |
| 2004/0259026 A1 | 12/2004 | Honma et al. | 430/270.1 |

FOREIGN PATENT DOCUMENTS

| | | |
|---|---|---|
| JP | 11-187900 | 7/1999 |
| JP | 11-340129 | 12/1999 |
| JP | 2002-324966 | 11/2002 |
| JP | 2002-327046 | 11/2002 |
| JP | 2002-328093 | 11/2002 |
| JP | 2003-7459 | 1/2003 |
| JP | 2003-11312 | 1/2003 |

OTHER PUBLICATIONS

Marjan Nienke Kraak et al., "In vivo Activities of Granule-Bound Poly[(R)-3-hydroxyalkanoate] Polymerase C1 of *Pseudomonas oleovorans*: Development of an Activity Test for Medium-Chain-Length-Poly(3-hydroxyalkanoate) Polymerases," 250 *Eur. J. Biochem*. 432-39 (1997).

Q. Qi et al., "In vitro Synthesis of Poly(3-hydroxydecanoate); Purification and Enzymatic Characterization of Type II Polyhydroxyalkanoate Synthases PhaC1 and PhaC2 from *Pseudomonas aeruginosa*," 54 *Appl. Microbiol. Biotechnol*. 37-43 (Jul. 2000).

John L. Speier et al., "The Addition of Silicon Hydrides to Olefinic Double Bonds. Part I. The Use of Phenylsilane, Diphenylsilane, Phenylmethylsilane, Amylsilane and Tribromosilane," 78 *J. Amer. Chem. Soc*. 2278-81(1956).

Dale A. Pelletier et al., "2-Hydroxycyclohexanecarboxyl Coenzyme A Dehydrogenase, an Enzyme Characteristic of the Anaerobic Benzoate Degradation Pathway Used by *Rhodopseudomonas palustris*" 182 (10) *J. Bacteriol*. 2753-60 (May 2000).

* cited by examiner

*Primary Examiner*—Herbert J. Lilling
(74) *Attorney, Agent, or Firm*—Fitzpatrick, Cella, Harper & Scinto

(57) ABSTRACT

A process for forming a fine pattern comprised of a polyhydroxyalkanoate on a substrate is provided. The process comprises steps of applying a polyhydroxyalkanoate-synthesizing enzyme and a 3-hydroxyacyl CoA to coexist in an intended pattern on a substrate, and polymerizing the 3-hydroxyalkanoate by action of the enzyme to form the polyhydroxyalkanoate in a pattern on the substrate. In particular, the fine pattern can be formed by an inkjet system.

11 Claims, No Drawings

PROCESS FOR FORMATION OF PATTERN OF POLYHYDROXYALKANOATE

BACKGROUND OF THE INVENTION

1. Field of the Invention

The present invention relates to a process for forming a fine pattern constituted of a polyhydroxyalkanoate on a substrate. Particularly, the present invention relates to a process for forming a fine pattern constituted of a polyhydroxyalkanoate by an inkjet system.

2. Related Background Art

Fine pattern-forming techniques such as lithography, which have been developed for production of integrated semiconductor circuits, are utilized for production of liquid crystals, electronic parts, and like articles, and further are employed as fine working technique such as MEMS. With the expansion of the application fields thereof, improvement of the technique is demanded for producing the fine patterns more simply at a lower cost.

In recent years, fine patterning techniques employing an inkjet system are attracting attention. The inkjet system has been developed as an ink ejection mechanism of a printer for ejecting an ink onto desired spots on a paper sheet to print letters or to draw a picture. The inkjet system ejects fine liquid droplets onto desired spots with high precision. By the inkjet system, a pattern can be formed in a line width of micron meters by ejecting a patterning material on a substrate.

For example, Japanese Patent Application Laid-Open No. H11-340129 describes formation of a resist pattern by ejecting a solution of a resist material through an inkjet head onto a pattern formation surface.

Japanese Patent Application Laid-Open No. 2002-324966 describes drawing of a circuit pattern on a wiring substrate by ejecting an electroconductive metal paste by an inkjet system.

On the other hand, high polymers capable of constructing various chemical structures are very useful and indispensable in industries and daily lives. Furthermore, the high polymers are promising because of the characteristics such as durability, shielding ability, insulating property, reactivity, and so forth.

For formation of a fine pattern from such a high polymer, the aforementioned inkjet system is investigated. Specifically, the high polymer is firstly dissolved in a solvent to prepare an ejection liquid composition for the inkjet system; this ejection liquid composition is ejected through an inkjet head onto a substrate; and the solvent of the ejected liquid is dried to obtain a pattern of the high polymer. In this method, the organic solvent is indispensable for dissolving the high polymer.

However, the organic solvent generally has a low surface tension to wet the substrate, so that the liquid droplets ejected onto the substrate can flow undesirably on the surface of the substrate to spread the pattern, making difficult the formation of the fine pattern. Further, in ejection by the inkjet system, the ejection accuracy can be decreased. For example, the ejection liquid composition having a surface tension of lower than 3 mN/m (=30 dyn/cm) can wet more the periphery of the nozzle opening to cause deviation of the trajectory of the liquid droplets.

To prevent the undesirable spreading of the pattern on the substrate or decrease of the ejection accuracy, the concentration of the high polymer in the ejection liquid composition may be increased to increase the viscosity of the ejection liquid composition. However, the increase of viscosity may prevent smooth ejection of the liquid composition through the ejection nozzle of the ink head, or may prevent sharp cutting of the ejection of the liquid composition at the ejection nozzle, or may cause threading of the ejected liquid between deposited dots on the substrate. For example, an ejection liquid composition having a viscosity higher than 20 cp is not ejected smoothly to cause frequently clogging of the nozzle, or does not form stable meniscus at the nozzle tip to make difficult the control of ejection quantity or ejection timing.

Furthermore, the organic solvent has a high volatility disadvantageously. For example, the organic solvent of the composition can evaporate to deposit the polymer around the ejection nozzle and to change the quantity or direction of the ejection to deviate the liquid deposition position or to cause clogging of the nozzle.

In use of the organic solvent, the ink head should be resistant to the solvent, and a ventilation apparatus should be equipped for evaporation of the organic solvent, which causes increase the cost.

To offset the above disadvantages, Japanese Patent Application Laid-Open No. 2003-7459 discloses an aqueous solution as the ejection liquid by employing a water-soluble medium compound of 20 or less molecules as the constituting material, but it does not mention a polymer of a higher molecular weight.

SUMMARY OF THE INVENTION

The present invention intends to solve the above problems, and provides a process for forming simply a fine pattern of a high polymer compound. In particular, the present invention intends to provide a process for forming a fine pattern of a high polymer compound by an inkjet system.

The present invention forms an intended pattern of a polyhydroxyalkanoate by allowing a polyhydroxyalkanoate-synthesizing enzyme and 3-hydroxyacyl CoA to coexist in an intended pattern and then polymerizing the 3-hydroxyacyl CoA by aid of the enzyme to synthesize polyhydroxyalkanoate in a pattern on the substrate. Here the term "CoA" is abbreviation of coenzyme A.

According to an aspect of the present invention, there is provided a process for forming a pattern comprised of a polyhydroxyalkanoate on a substrate, the process comprising the steps of:

making a polyhydroxyalkanoate-synthesizing enzyme and a 3-hydroxyacyl CoA coexist with each other in an intended pattern on a substrate, synthesizing the polyhydroxyalkanoate by polymerizing the 3-hydroxyalkanoate CoA by action of the enzyme.

The process preferably further comprises the step of applying a solution containing the polyhydroxyalkanoate-synthesizing enzyme and the 3-hydroxyacyl CoA to the substrate in an intended pattern to synthesize the polyhydroxyalkanoate in the solution. The solution preferably includes a first solution containing a polyhydroxyalkanoate-synthesizing enzyme and no 3-hydroxyalkanoate, and a second solution containing a 3-hydroxyalkanoate and no polyhydroxyalkanoate-synthesizing enzyme; and one of the first solution and the second solution is firstly applied to the substrate, and then the other solution is applied onto the firstly applied solution.

After the synthesizing step, the making step for coexistence and the synthesizing step are preferably repeated.

The process preferably further comprises a step of drying the substrate after the synthesizing step.

The process preferably further comprises a step of heating the substrate up to a temperature higher than the glass transition temperature of the synthesized polyhydroxyalkanoate after the synthesizing step.

The process preferably further comprises the step of decomposing at least a portion of the pattern comprised of the polyhydroxyalkanoate by a polyhydroxyalkanoate-decomposing enzyme. The step of decomposing at least a portion of the pattern preferably comprises applying a solution containing the polyhydroxyalkanoate-decomposing enzyme to a portion to be decomposed on the pattern comprised of the polyhydroxyalkanoate to carry out the decomposition of the polyhydroxyalkanoate in the solution.

The process preferably further comprises a step of fixing a nucleic acid or a protein onto the pattern comprised of the polyhydroxyalkanoate. The fixing step preferably comprises covalent bond formation between a reactive group of the polyhydroxyalkanoate and a reactive group of the nucleic acid or protein. The reactive group of the polyhydroxyalkanoate is preferably at least one selected from the group consisting of epoxy, vinyl, bromo and carboxyl, and the reactive group of the nucleic acid or protein is preferably at least one selected from the group consisting of amino and thiol.

The process preferably further comprises a step of modifying chemically at least a part of the pattern comprised of the polyhydroxyalkanoate. The polyhydroxyalkanoate preferably has at least a monomer unit having a reactive group, and the reactive group is preferably used as an active site in the chemically modifying step. The reactive group is preferably at least one selected from the group consisting of epoxy, vinyl, bromo and carboxyl.

The process preferably further comprises a step of producing the polyhyroxyalkanoate-synthesizing enzyme by employing a microorganism having an ability to produce the enzyme. The microorganism is preferably comprised of a transformant having a gene relating to the ability to produce the polyhydroxyalkanoate-synthesizing enzyme. The gene is preferably derived from a microorganism having the ability to produce the polyhydroxyalkanoate-synthesizing enzyme. The host microorganism of the transformant is preferably *Escherichia coli*.

According to another aspect of the present invention, there is provided a substrate comprising a pattern comprised of a polyhydroxyalkanoate formed thereon.

In the method of the present invention, the solution applied to the substrate contains neither a high polymer nor an organic solvent, so that a fine pattern can readily be conducted effectively by an inkjet system. The polyhydroxyalkanoate can be selected from those having various chemical structures and containing a highly reactive substituent, which enables multiple function of the polyhydroxyalkanoate pattern by functional group introduction or chemical conversion.

DESCRIPTION OF THE PREFERRED EMBODIMENTS

A process of a typical embodiment of the present invention comprises a first step of applying a solution containing a polyhydroxyalkanoate-synthesizing enzyme and 3-hydroxyacyl CoA, or applying a solution containing a polyhydroxyalkanoate-synthesizing enzyme and a solution containing 3-hydroxyacyl CoA simultaneously or separately on a substrate to allow the both substances to coexist in an intended pattern; and a second step of a polyalkanoate synthesis reaction in the solution deposited in the pattern.

(Polyhydroxyalkanoate)

In the present invention, a polyhydroxyalkanoate is used as the pattern-constituting high polymer material. Generally the polyhydroxyalkanoate (hereinafter occasionally referred to as "PHA") is attracting attention as a biodegradable plastic material and a non-petroleum-derived polymer. The PHAs are being investigated actively as functional high polymers since various functional groups can be introduced to the side chain.

The PHA for the pattern formation on a substrate according to the present invention is not specially limited, provided that the PHA can be synthesized by a PHA-synthesizing enzyme from 3-hydroxyacyl CoA as the substrate.

The synthesis of the PHA by a PHA-synthesizing enzyme is explained below briefly.

A certain PHA-producing microorganism synthesizes (R)-3-hydorxyacyl CoA from a carbon source or an alkanoic acid through a metabolic pathway in vivo (e.g., a β-oxidation system, and a fatty acid synthesis pathway), and synthesizes, from it as the substrate, a PHA by polymerization with a PHA-synthesizing enzyme (called also PHA polymerase, or PHA synthase; hereinafter referred to occasionally as "PHA synthase") to accumulating the PHA in the cells.

The biosynthesizable PHA includes PHAs comprised of 3-hydroxyalkanoic acid units having a short chain length of 0 to 2 carbons (hereinafter referred to occasionally as "scl-PHA"), PHAs comprised of 3-hydroxyalkanoic acid units having a medium chain length having 3 to 12 carbons (hereinafter referred to occasionally as "mcl-PHA"), and PHAs having on the side chains a substituent other than the alkyl, such as groups of phenyl, phenoxy, cyclohexyl, unsaturated hydrocarbon, ester, allyl, cyano, halogenated hydrocarbon, and epoxide (hereinafter referred to occasionally as "unusual-PHA").

The scl-PHA-synthesizing enzyme is called a PHB-synthesizing enzyme (also called a PHB polymerase, or PHB synthase). This enzyme is included in the PHA-synthesizing enzyme in the present invention.

The PHA can be synthesized also in vitro by taking out the aforementioned PHA-synthesizing enzyme from the PHA-forming bacterium cells, and polymerizing a 3-hydroxyacyl CoA as the substrate by the PHA-synthesizing enzyme.

The inventors of the present invention disclose utilization of the in-vitro PHA synthesis for coating a base material such as fine particles (Japanese Patent Application Laid-Open Nos. 2002-327046, and 2003-011312). In this method, the PHA-synthesizing enzyme is immobilized on the base material surface by dispersing or immersing the base material in a PHA-synthesizing enzyme solution, and thereto 3-hydroxyacyl CoA is added to synthesize a PHA on the base material surface for coating.

The present invention also utilizes the in-vitro PHA synthesis. However, in the present invention, the PHA-synthesizing enzyme and the 3-hydroxyacyl CoA are allowed to coexist in a pattern on a substrate, and the PHA is synthesized in a pattern. This process is different from the above-mentioned disclosed method. The disclosed method does not mention the fine patterning of the present invention.

The PHA synthesized in the patterning process according to the present invention has preferably a number-average molecular weight ranging preferably from about 10,000 to about 10,000,000 in order to obtain strength of the pattern.

(3-Hydroxyacyl CoA)

The 3-hydroxyacyl CoA useful in the present invention is not limited, provided that it is polymerizable by the PHA-synthesizing enzyme. The chemical structure of the PHA for the patterning can be controlled by suitably selecting the 3-hydroxyacyl CoA.

The 3-hydroxyacyl CoA to be used can be synthesized by a method selected from in-vitro synthesis methods employing an enzyme; in-vivo synthesis methods employing a living matter such as microorganisms, and vegetables; and chemical synthesis methods. In particular, the enzymatic synthesis methods are utilized generally for synthesis of the substrate. A known method is synthesis of 3-hydroxyacyl CoA from 3-hydroxyalkanoic acid and CoA by using commercial acyl CoA synthetase (acyl CoA ligase, E.C.6.2.1.3.) (Eur. J. Biochem., 250, 432-439 (1997); Appl. Microbiol. Biotechnol., 54, 37-43 (2000).

(PHA-Synthesizing Enzyme)

The PHA-synthesizing enzyme in the present invention may be the one produced by a microorganism capable of producing the enzyme, or produced by a transformant having a gene of a PHA-synthesizing enzyme of the microorganism introduced therein.

The microorganism capable of producing the PHA-synthesizing enzyme includes microorganisms capable of producing mcl-PHA or unusual PHA such as *Pseudomonas* sp., *Burkholderia* sp., *Aeromonas* sp., and *Comamonas* sp. Specific examples are *Pseudomonas putida* P91, *Pseudomonas cichorii* H45, *Pseudomonas cichorii* YN2, *Pseudomonas jessenii* P161, *Burkholderia* sp. OK3 (FERM P-17370), and *Burkholderia* sp. OK4 (FERM P-17371) which have been isolated by the inventors of the present invention.

The microorganism capable of producing the scl-PHA includes *Aeromonas* sp., *Alcaligenes* sp., *Chromatium* sp., *Comamonas* sp., *Methylobacterium* sp., *Paracoccus* sp., and *Pseudomonas* sp. Specific examples are *Burkholderia cepacia* KKO1 (FERM BP-4235), *Ralstonia eutropha* TB64 (FERM BP-6933), and *Alcaligenes* sp. TL2(FERM BP-6913) which have been isolated by the inventors of the present invention.

The above specifically mentioned microorganisms have been respectively deposited for international deposition to Patent Organism Depository Center of National Institute for Industrial Technology (independent administrative corporation) according to Budapest Treaty (on the International Recognition of the Deposit of Microorganism for the Purpose of Patent Procedure) as follows: P91, FERM BP-7373 (deposit number); H45, FERM BP-7374; YN2, FERM BP-7375; P161, FERM BP-7376; OK3, FERM P-17370; OK4, FERM P-17371; KK01, FERM BP-4235; TB64, FERM BP-6933; and TL2, FERM BP-6913.

The PHA-synthesizing enzyme can be prepared by using a transformant having a PHA-synthesizing enzyme gene of the aforementioned PHA-synthesizing enzyme. The cloning of the PHA synthesizing enzyme gene, preparation of the expression vector, and preparation of the transformant can be conducted by conventional manners.

The cultivation of the microorganism for preparation of the PHA-synthesizing enzyme of the present invention may be conducted by any method which can express the PHA-synthesizing enzyme in the microorganism body. The culture medium is not limited, provided that the above conditions are satisfied.

Specifically, the PHA-synthesizing enzyme can be prepared by growing a PHA-producing microorganism in an inorganic culture medium like M9 culture medium containing an alkanoic acid such as octanoic acid and nonanoic acid, a phosphorus source, and a nitrogen source, and further containing a micro component like a mineral by aeration cultivation.

When the transformant or the PHA-producing microorganism has antibiotic resistance, the cultivation may be conducted with a culture medium containing a corresponding antibiotic to prevent microbial contamination.

When an inducing promoter is used for the transformant expression vector, an inducer corresponding to the promoter may be added to the culture medium to promote the expression of the PHA-synthesizing enzyme. The inducer is exemplified by isopropyl-β-D-thiogalactopyranside (IPTG), tetracycline, and indole-acrylic acid (IAA).

The cultivation temperature is not limited insofar as the microorganism can grow satisfactorily, ranging preferably from 15° C. to 40° C., more preferably from 20° C. to 35° C.

The PHA-synthesizing enzyme can be prepared through steps of cultivating the aforementioned PHA-producing microorganism to grow the concentration of the microorganism and to accumulate the PHA-synthesizing enzyme in the microorganism cells; recovering the microorganism from the liquid culture medium by centrifugation, filtration, or a like method; crushing the microorganism cells by a French press, ultrasonic crushing, freezing-and-thawing, or by use of lisozyme or a surfactant; and recovering the accumulated PHA-synthesizing enzyme from the microorganism cells.

The state of the PHA-synthesizing enzyme to be used may be the crushed microorganism dispersed in a liquid, a crude enzyme precipitated and recovered as a protein by ammonium sulfate or the like, or a purified enzyme obtained by a purification procedure.

The purification of the PHA-synthesizing enzyme may be conducted by any procedure, provided that the enzymatic activity of the PHA-synthesizing enzyme is retained after the purification. For example, from a crude enzyme, a purified enzyme can be obtained by affinity chromatography, anion or cation exchange chromatography, gel filtration, or a like method, or combination thereof. In particular, when the PHA-synthesizing enzyme is expressed as a recombinant protein, it is expressed in a form of a fused protein having a tag like a histidine residue on the N terminal or C terminal thereof, and the protein can be purified simply by bonding through the tag to an affinitive resin. Such a fusion protein includes, in addition to the histidine tag, glutathione S-transferase (GST), chitin-bonded domain (CBD), maltose-bonded protein (MBP), and thio-redoxin (TRX).

The objective protein can be isolated from the fused protein by cleavage by a protease such as thrombin and a blood coagulation factor Xa, lowering of the pH level, addition of imidazole as a competitive bonding agent in a high concentration, or a like method. Otherwise, when the tag contains intein as in the case where pTYB1 (produced by New England Biolab Co.) as the expression vector, the cleavage is conducted with dithiothreitol or the like under reductive conditions.

The PHA-synthesizing enzyme may be used with a stabilizer or an activator such as a metal salt, glycerin, dithiothreitol, EDTA, bovin serum alubumin (BSA), and molecular chaperone, as necessary.

The activity of the PHA-synthesizing enzyme can be measured by any of known methods. For example, the CoA released in the process of polymerization of 3-hydroxyacyl CoA by the catalytic action of the PHA-synthesizing enzyme is measured by the color developed with 5,5'-dithio-bis(2-nitrobenzoic acid) in principle. The method is more specifically described below. The reagents employed are as follows: Reagent-1, bovin serum albumin (Sigma Co.) is dissolved at a concentration of 3.0 mg/mL in a 0.1 mol/L tris-HCl buffer (pH 8.0); Reagent-2, 3-hydroxyoctanoyl CoA is dissolved at a concentration of 3.0 mmol/L in a 0.1 mol/L tris-HCl buffer (pH 8.0); Reagent-3, trichloroacetic acid is dissolved at a concentration of 10 mg/mL in a 0.1 mol/L tris-HCl buffer (pH 8.0); Reagent-4,5,5'-dithio-bis(2-nitrobenzoic acid) is dissolved at a concentration of 2.0 mmol/L in a 0.1 mol/L tris-HCl buffer (pH 8.0). For the measurement, the reactions are allowed to proceed in two reaction steps as below. In the first reaction (PHA synthesis reaction), to 100 μL of the sample solution (enzyme solution), is added and mixed 100 μL of Reagent-1, and the resulting mixture is pre-incubated at 30° C. for one minute. Thereto, 100 μL of Reagent-2 is added and mixed, and the mixture is incubated at 30° C. for 1 to 30 minutes. Then Reagent-3 is added thereto to stop the reaction. In the second reaction (development of color by the released CoA), the first reaction solution after stop of the reaction is centrifuged at 147 km/s$^2$ (=15,000×g) for 10 minutes. To 500 μL of the supernatant, is added 500 μL of Reagent-4, and the mixture is incubated at 30° C. for 10 minutes. After the incubation, the absorbance is measured at 412 nm. The unit of enzymatic activity: the quantity of the enzyme to release 1 μmol of CoA in one minute is defined as one unit (U).

(Solution Applied to Substrate)

In the first step of the present invention, a solution or solutions containing the PHA-synthesizing enzyme and 3-hydroxyacyl CoA are applied to the substrate by a solution-applying method such as an inkjet system to form an intended pattern of a solution containing the two substances in coexistence.

The solution used in this step (hereinafter referred to occasionally as a "patterning solution") may be one solution containing the PHA-synthesizing enzyme and 3-hydrocyacyl CoA, or may be two solutions, one solution containing the PHA-synthesizing enzyme and another solution containing 3-hydroxyacyl CoA. Furthermore, two or more solutions may be used which contains different kinds of 3-hydroxyacyl CoA respectively.

With a patterning solution containing both of the PHA-synthesizing enzyme and 3-hydroxyacyl CoA, one application operation is sufficient to allow the PHA-synthesizing enzyme and 3-hydroxyacyl CoA to coexist on the substrate. With a patterning solution containing the PHA-synthesizing enzyme and another patterning solution containing 3-hydroxyacyl CoA, the solutions should be mixed on the substrate. The method of application of the patterning solution or solutions is described later in detail.

The concentration of the PHA-synthesizing enzyme or 3-hydrocyacyl CoA in the patterning solution is selected depending on the time for synthesizing the PHA, and the film thickness of the PHA to be patterned. However, an excessive high concentration increases the viscosity of the patterning solution to make possibly the application of the solution difficult. Therefore, the PHA-synthesizing enzyme is contained, in 1 mL of the patterning solution, at a concentration ranging preferably from 10 units (U) to 1000 units (U), more preferably from 100 units (U) to 500 units (U). The 3-hydroxyacyl CoA is contained usually at a concentration ranging from 0.1 mol/L to 2 mol/L, preferably from 0.5 mol/L to 1 mol/L.

The patterning solution may further contain any additive that does not retard the activity of the PHA-synthesizing enzyme and does not retard the application of the patterning solution onto the substrate. In particular, for stabilizing the activity of the PHA-synthesizing enzyme and causing the PHA synthesis reaction suitably, the solution contains preferably an inorganic or organic salt or the like to give a buffering ability to the solution.

The composition of the buffered solution may be selected for the pH range employed. Any component may be added insofar as it does not impair the activity of the PHA-synthesizing enzyme and does not retard the application of the patterning solution to the substrate. For example, there may be added a usual buffering agent such as an acetate buffer, a phosphate buffer, a potassium phosphate buffer, a 3-(N-morpholino)propanesulfonic acid buffer (MOPS), an N-tris(hydroxymethyl)methyl-3-aminopropanesulfonic acid buffer (TAPS), a tris-hydrochloric acid buffer, a glycine buffer, and a 2-(cyclohexylamino)-ethanesulfonic acid buffer (CHES).

The concentration of the buffer solution is not specially limited provided that the activity of the PHA-synthesizing enzyme employed is not impaired. The concentration ranges usually from 5.0 mmol/L to 1.0 mol/L, preferably from 0.1 mol/L to 0.2 mol/L.

The suitable pH to be adjusted by the buffer solution ranges from pH 5.5 to pH 9.0, preferably from pH 7.0 to pH 8.5. Depending on the property of the PHA-synthesizing enzyme, the pH may be outside the above-mentioned range.

In the case where the patterning solution may possibly be contaminated by a microorganism, an antiseptic agent or the like is preferably added thereto to inhibit the growth of the microorganism.

The patterning solution contains also preferably an evaporation-preventing component such as a moisturizing agent for prevention of evaporation or drying of the patterning solution during the synthesis reaction on the substrate.

When a thermal inkjet method as the inkjet system is employed in which the solution is heated for liquid ejection, a polyhydric alcohol like glycerin, or oligosaccharide, or the like may be added to prevent thermal denaturation of the PHA-synthesizing enzyme or the monomer which may be caused by the high temperature for the ejection.

The patterning solution to be applied to the substrate is an aqueous solution, and does not contain a polymer compound as the component as mentioned above in the present invention. Therefore, the solution is ejected smoothly by an inkjet system. The properties of the solution are preferably adjusted further for more efficient ejection by the inkjet system. For example, in a thermal inkjet system, addition of a water-soluble alcohol like ethanol, isopropyl alcohol, and a lower alkyl ether of a polyhydric alcohol stabilizes the bubbling of the solution on a thin film resistance in the ejection orifice of the inkjet head. The viscosity of the solution is adjusted preferably in the range from 1 to 20 mPa·s (cps). The surface tension is adjusted preferably to be not lower than 3 mN/m (=30 dyn/cm). With the viscosity ranging from 1 to 5 mPa·s (cps) and the surface tension ranging from 3 to 5 mN/m (=30-50 dyn/cm), the solution is deposited very precisely at the intended spots, and the shape of the spot formed on the substrate by the solution ejection is circular without spreading of the spot to draw precisely a pattern, advantageously. In the present invention, since the solution to be ejected by an inkjet system is an aqueous solution, the properties of the solution can relatively easily be adjusted to be within the above range.

The properties of the solution are adjusted as described above for efficient ejection by an inkjet system. When the patterning solution is applied onto the substrate by a method other than the inkjet system, or when a pattern need not be strictly precise even though the solution is applied by an inkjet system, the properties of the patterning solution are not limited to be in the above range.

(Substrate)

The substrate in any shape and of any material is useful, in the present invention, which is capable of accepting the patterning solution and holding the pattern of the solution adhering to the substrate after the application of the patterning solution on the substrate, and does not contain a substance inhibiting the reaction of the PHA-synthesizing enzyme, enabling the PHA-synthesizing reaction by the PHA-synthesizing enzyme. The shape of the substrate is not limited to be a flat plate, but may be curved, uneven, or in any shape, provided that the applied patterning solution is not movable with the shape and material of the substrate. The material of the substrate may be of any kind, including high polymer compounds and inorganic solids such as glass, resins, and metals, or may be a material which allows the applied solution to penetrate into the substrate, such as paper sheets. The surface of the substrate may preliminarily be treated chemically, physically, or by radiation rays, or by application of a polymer material or a silane coupling agent.

When a water-repellant substrate is used, the substrate is preferably flat, and is preferably placed horizontally before completion of the PHA synthesis process.

Before the treating steps of the present invention, the substrate may be treated for sterilization. The sterilization prevents undesired decomposition of the PHA-synthesizing enzyme, consumption of the monomer, formation of PHA synthesis reaction inhibitor in the solution by action of an intruding microbe. The sterilization may be conducted by any method which does not change the properties of the substrate, and may be conducted by irradiation of active rays such as UV ray; washing with a disinfectant such as alcohol.

(Method of Application of Solution on Substrate)

As mentioned above, the patterning solution can be applied to the substrate by an inkjet system effectively with efficient ejection performance. However, the method of application is not limited to the inkjet system. Any other method of the solution application can be employed suitably since the patterning solution applied to the substrate in the present invention is an aqueous solution containing no high polymer compound.

Other than the inkjet system, for the solution application, any method may be employed which is capable of applying a patterning solution to the substrate. For fine pattern formation, a micro quantity feeding system is useful, such as micropipette systems, micro dispenser systems, pin systems, and capillary systems.

The pin system brings a pin tip into contact with the surface of a sample-containing solution to pick up a portion of the solution, and then brings the tip into contact mechanically with the substrate to apply the sample solution onto the substrate.

The capillary system sucks a sample solution into a capillary, and applies the sample solution to a substrate from the tip of the capillary by mechanical contact of the capillary tip with the substrate.

Any of the above-mentioned systems is useful for applying the patterning solution to the substrate. Of these systems, the inkjet system is particularly useful, since the apparatus is inexpensive and readily available and a micro quantity of the patterning solution can simply be applied onto any intended positions on the substrate. Among the inkjet systems, a thermal inkjet system and a piezo inkjet system are suitably employed. The thermal inkjet system ejects liquid droplets by driving force generated by bubble formation by heating. The piezo inkjet system ejects the ink droplets by displacement of a piezo element.

The inkjet system usually has a driving device for driving an inkjet head to any position on the substrate and a control device for controlling ejection conditions of the liquid through the inkjet head and controlling the movement of the inkjet head driven by the driving device. The inkjet system applies the patterning solution in a pattern onto the substrate according to information input to the control device: the information including a pattern shape, a quantity of an applied liquid droplet, and times of the application.

The amount of the patterning solution to be applied to the substrate is not limited specially, but should be in the range not to cause spreading of the liquid droplets outside the prescribed pattern line. In the inkjet system, the amount of one liquid droplet can be controlled to be not larger than 100 pL for pattern drawing with high precision.

The film thickness of the patterned PHA can be controlled by adjusting the concentrations of the PHA-synthesizing enzyme and 3-hydroxyacyl CoA and adjusting the amount of depositing liquid droplets per unit area of the pattern formation face. The amount of the deposited liquid droplets can be adjusted by controlling the times of repetition of the liquid droplet deposition per unit area of the pattern formation face, by controlling the pitches between the liquid droplets deposited on the pattern formation face, or by controlling the amount of the liquid droplets in one deposition.

The amount of deposition of the solution on a certain pattern formation face has an upper limit. The thickness of the PHA pattern coating film can be increased, after the PHA synthesis in a pattern and removal of the solvent by drying, repeating the application of the patterning solution on the same pattern face, synthesis of PHA, and drying of the solvent.

In the case where the PHA-synthesizing enzyme and 3-hydroxyacyl CoA are contained in one patterning solution, the PHA-synthesizing enzyme and 3-hydroxyacyl CoA are allowed to coexist on a substrate at least by one application operation, as mentioned above.

However, if the enzyme-CoA mixture solution is brought unintentionally to a temperature condition for PHA synthesis, the PHA comes to be synthesized in the solution before the solution is applied to the substrate plate. This tends to cause clogging of nozzle on ejection by an inkjet system, impairing the effect of the present invention. Therefore, the enzyme-CoA solution is preferably kept cooled, during the time from mixture preparation to application to the substrate, at a low temperature where the PHA synthesis will not be caused. The cooling temperature ranges preferably from 0° C. to 10° C., more preferably from 2° C. to 5° C.

In the case where the PHA-synthesizing enzyme and the 3-hydroxyacyl CoA are dissolved separately as the patterning solutions, the two solutions are applied independently to a pattern face on a substrate, and are allowed to mix together for the coexistence of the PHA-synthesizing enzyme and the 3-hydorxyacyl CoA. By this method, the respective solutions will not cause PHA synthesis reaction even if the solutions are separately brought to the PHA synthesis conditions. Therefore, the solutions need not be cooled or kept off of the synthesis-causing conditions. However, the solutions may be cooled similarly as above to prevent deactivation of the PHA-synthesizing enzyme or contamination of the solutions by microorganism.

The respective patterning solutions containing the PHA-synthesizing enzyme or the 3-hydroxyacyl CoA are applied independently onto a substrate in a manner as mentioned below. By an inkjet system, for example, the respective solutions are placed in separate ink tanks, and one solution is firstly applied through a nozzle onto a substrate, and then the other solution is applied through another nozzle onto the pattern of the first solution in superposition. Otherwise, the respective solutions are applied to the substrate simultaneously, or the solutions are mixed just before application to the substrate. Any of the above application methods is useful.

Otherwise, plural patterning solutions containing different compositions of 3-hydroxyacyl CoA are applied to a pattern face to prepare a pattern comprised of different monomer units locally in the pattern.

Here, the "different compositions of 3-hydroxyacyl CoA" signifies compositions containing different 3-hydroxyacyl CoA having a different chemical structure, or containing different kinds of 3-hydroxyacyl CoA at different concentrations thereof.

The aforementioned patterning solutions of different compositions may be applied onto separate pattern faces, or may be applied partly overlapping onto a part of the same pattern face in superposition. In superposing application, the solutions can be mixed to enable formation of PHA having plural monomer unit compositions.

The patterning solutions having different compositions can be applied, for example, by an inkjet system independently by using plural heads to a substrate.

By repeated PHA synthesis conducted by application of a patterning solution or solutions plural times on the same pattern face, as in the above-mentioned case of PHA film thickness control, a multilayered structure can be formed in which monomer unit composition of the PHA film varies in the thickness direction on a substrate by changing the kind, concentration, and composition of 3-hydorxyacyl CoA in the solution in each of applications.

In such a manner, a PHA pattern can be formed with a PHA less affinitive to a substrate. For the formation, firstly, PHA is formed from a 3-hyroxyacyl CoA for forming a PHA having high affinity to the substrate; then another PHA is formed thereon from a mixture with another 3-hydorxyacyl CoA as the source for the final surface PHA; and stepwise the final 3-hydroxyacyl CoA concentration is increased. Thus a PHA pattern can be formed which is bonded firmly to the substrate and has intended monomer unit composition.

(PHA Synthesis Reaction)

In the second step of the present invention, a PHA synthesis reaction is conducted in a solution adhering in a pattern formed in the first step.

The PHA synthesis reaction can be allowed to proceed by keeping the substrate at suitable temperature conditions.

The reaction temperature of the PHA synthesis reaction is suitably selected depending on the activity of the PHA-synthesizing enzyme employed, the activity retention time thereof, and so forth. The temperature ranges usually from 15° C. to 40° C., preferably from 20° C. to 35° C.

The reaction time depends on the thickness of the PHA pattern to be prepared, the stability of the PHA-synthesizing enzyme, and so forth, ranging usually from one minute to three days, preferably from 30 minutes to 12 hours.

During the PHA synthesis reaction, the substrate is preferably kept in a suitably controlled environmental humidity conditions so as to prevent evaporation of the patterning solution adhering onto the substrate or conversely not to cause moisture condensation.

The synthesized PHA are in a shape of particles, having diameters ranging from several nanometers to several microns, occasionally aggregates into blocks or flocks, and disperses in the patterning solution or precipitates and deposits on the substrate.

(Post-Treatment Step)

The synthesized PHA is further post-treated for satisfactory pattern formation.

After the PHA synthesis in the patterning solution on the substrate, an excess of the patterning solution is removed by drying. The drying may be conducted by any method, provided that the synthesized PHA and the substrate are not denatured or not deformed. The drying method includes removal of water by centrifugation such as spin drying, heating, pressure reduction, standing left in low-humidity atmosphere, blowing of dry gas, and contact with water-absorbent material, and combination of the above methods.

After the drying step, washing may be conducted to remove a solute component of the patterning solution. The washing may be conducted in any method, provided that the PHA fixed on the substrate is not exfoliated. For example, the washing may be conducted by addition of a cleaning agent such as water, a buffer solution, and methanol which does not dissolve the pattern-forming PHA, or by immersion of the substrate in the cleaning agent. After the washing, the substrate is preferably dried again.

By the above drying operation, the PHA pattern formation is completed on the substrate. In this state, many PHA particles are deposited in a state of layers on the pattern face on the substrate. For improvement of the coating properties and shielding properties of the pattern face, heat treatment may be conducted to fuse the laminated PHA particles into one coating film. The heat treatment temperature depends on the Tg of the PHA. A PHA having a chemical structure of lower Tg can be treated effectively at a relatively low temperature, for example, in the range from 60 to 80° C. The above-mentioned drying step may be conducted by heat treatment for simultaneous drying and film formation.

In the above drying step, the PHA is fixed firmly in a certain extent onto the substrate. In the case where the PHA and the substrate are both hydrophobic, the both are bonded relatively firmly by hydrophobic bonding to render the additional fixation treatment unnecessary. However, in this case also, the fixation treatment may be conducted depending on the kinds, structures and uses of the PHA and the substrate. The chemical structure of the PHA may be selected for the fixation treatment.

For example, a PHA having a low Tg can be fusion-bonded by heat treatment to a surface of a substrate. To an electrified substrate surface, a PHA having a functional group electrifiable with an opposite electric charge can be fixed by ionic adsorption. A non-electrifiable substrate can be made electrifiable by bonding, to the substrate, an electrifiable substance such as fine particles of a metal or inorganic oxide, a cationic polymer, and an anionic polymer.

(Chemical Modification)

After the aforementioned post-treatment, the PHA may be treated for chemical modification to obtain a PHA pattern having more useful functions and characteristics.

For example, introduction of a graft chain to a PHA gives a PHA pattern having useful characteristics resulting from the graft chain. Cross-linking of a PHA gives a PHA pattern having higher mechanical strength, higher chemical resistance, higher heat resistance, or the like.

The chemical modification may be conducted by any method which does not denature or deform the PHA and the substrate: for example, a PHA having a functional group on a side chain is synthesized and the functional group is utilized for chemical modification.

The reactive functional group is exemplified by an epoxy group. A PHA having an epoxy group on a side chain can be chemically converted in the same manner as an ordinary polymer having an epoxy group. For example, the epoxy group can be converted to a hydroxyl group; a sulfonic group can be introduced thereto; or a thiol or amine can be bonded thereto. A graft chain can be introduced to a PHA by reaction of the epoxy group with a compound having a terminal reactive functional group such as an amino group reactive to the epoxy group.

The compound having a terminal amino group is exemplified by polyvinylamine, polyethylenimine, and amino-modified polymers such as amino-modified polysiloxane (amino-modified silicone oil). The amino-modified polysiloxane may be a commercial modified silicone oil, or may be synthesized according to the method described in J. Am. Chem. Soc., 78, 2278 (1956), and so forth.

Another example of chemical conversion of a PHA having an epoxy group is cross-linking by a diamine compound such as hexamethylenediamine; succinic anhydride; 2-ethyl-4-methylimidazole; electron ray irradiation; and so forth.

Another example of the functional group other than the epoxy group is a vinyl group. The vinyl group can combine with a compound having a thiol group. The vinyl group can be converted to a carboxyl group by use of an oxidizing agent such as potassium permanganate. The vinyl group can be converted to an epoxy group by chloroperbenzoic acid. Further, the group can be used for a intramolecular crosslinking reaction.

Still another example of the reactive functional group is a bromo group. This group is also useful for addition of a compound having a thiol group.

(Working of Pattern by Decomposition of PHA)

A part or the whole of a PHA pattern formed on a substrate can be decomposed and removed from the substrate. The method of decomposition of the PHA includes elution by an organic solvent capable of dissolving the PHA, hydrolysis by addition of an acid or an alkali and heating, and enzymatic decomposition by a PHA-decomposing enzyme. Of these methods, by use of the PHA-decomposing enzyme, a PHA pattern can be decomposed in a micro region by a fine solution applying method used for application of a patterning solution to a substrate in the present invention, such as an inkjet system.

Thereby, for example, the PHA pattern can further be converted to a negative type one, or the pattern can be retouched. The PHA pattern of the present invention can be bonded to a nucleic acid or a protein as described later. By utilizing the nucleic acid or the protein, a target substance in a sample can be recovered by trapping by the nucleic acid or the protein and then decomposing the PHA having the nucleic acid or the protein.

The PHA-decomposing enzyme includes ester hydrolysis enzymes such as lipases, esterases, and PHA-depolymerases. The PHA-decomposing enzyme may be a commercial enzyme, or one derived from a microorganism like a bacterium or fungi capable of decomposing the PHA. The known microorganism includes genuses of *Alcaligenes, Pseudomonas, Comamonas, Rhodobacter, Rhodospirillum, Zoogloea,* and *Penicillium*; and *Rizopus delemer*. In particular, useful are PHA depolymerases produced by *Alcaligenes faecalis, Comamonas acidovorans, Pseudomonas picketii,* *Pseudomonas lemoignei, Pseudomonas testosteroni, Penicillium pinophilum*; and a lipase produced by *Rizopus delemer*.

The enzyme is preferably selected for the kind of the PHA to be decomposed since the above enzymes have a specificity to a medium.

The PHA-decomposing enzyme can be prepared in the same manner as in preparation of the PHA-synthesizing enzyme. When the enzyme is secreted out of the microorganism cells, the enzyme is recovered from the supernatant liquid of the culture.

The aforementioned PHA decomposition treatment is preferably conducted prior to the aforementioned chemical modification of the PHA. However, the decomposition may be conducted after the chemical modification, if possible.

(Analysis of Patterned PHA)

For confirmation of the pattern shape and composition of the PHA on the substrate, for example, composition analysis by gas chromatography or the like and shape observation by electron microscopy are combinedly conducted. The PHA pattern formed from a multi-layered coating film can be analyzed by time-of-flight secondary ion mass spectrometer (TOF-SIMS) and ion sputtering technique to identify the constituting layers.

For a more direct and simpler analysis, useful is combination of Nile Blue A dyeing and fluorescence microscopy observation which was developed by the inventors of the present invention (Japanese Patent Application Laid-Open No. 2002-328093). In this method, the substrate carrying a formed pattern is dyed with a fluorescent dye by the above method, and is observed under an exciting light by fluorescence microscopy to confirm the PHA pattern by a fluorescence-emission pattern. This method is useful for the PHA pattern shape evaluation in the present invention insofar as the used substrate is not fluorescent.

(Examples of Use of PHA Pattern According to Present Invention)

The pattern formation method of the present invention is useful for producing a sensor chip, a reaction chip, a detection array, and so forth in which a sensor element such as an enzyme, a catalyst element, and a probe such as a nucleic acid and a protein are effectively placed. Specifically, the PHA can be selected which has a chemical structure having a reactive functional group such as epoxy, vinyl, bromo, and carboxyl; and an enzyme having another functional group reactive to the above-mentioned functional group such as amino and thiol exposed on the surface or a nucleic acid probe having such a group introduced at the terminal is selectively immobilized onto the PHA; and the enzyme, the nucleic acid probe, or the like is placed in a pattern on the substrate.

The pattern formation method of the present invention is effective for production of an array pattern formation well for a matrix pattern for a display and a color filter or an array pattern for a DNA chip or a protein chip; production of partition wall for a microreactor or a fine flow channel in combinatorial chemistry. That is, the PHA formed on a substrate in a projection pattern can serve as a partition wall. Otherwise, the PHA pattern formed in a pattern with a certain area is decomposed by applying the above-mentioned PHA-decomposing enzyme to form a recess by decomposition of the PHA, and the recess is utilized for the above use.

For forming a black matrix for display or a color filter, a black dye or a black pigment is added to the patterning solution to form a light-intercepting partition wall.

Japanese Patent Application Lai-Open No. H11-187900 discloses probe array formation in which a water-repelling well is formed for holding a probe-containing solution on a substrate, ensuring dispensing and isolation of the probe solution. On the other hand, the PHA pattern prepared by the present invention also is effective for use as an array pattern formation well owing to the water-repellency thereof.

The PHA pattern and the method of formation thereof are not limited by the above description.

EXAMPLES

The present invention is explained below more specifically by reference to Examples. The Examples below are best embodiments of the present invention, but do not limit the technical range of the present invention thereto. The percentage (%) in the examples below is based on weight unless otherwise mentioned.

Reference Example 1

Production of PHA-Synthesizing Enzyme: 1

A PHA-synthesizing enzyme gene (YN2—C1) was derived from a YN2 strain by a conventional manner. The gene was inserted to the corresponding site of pGEX-6P-1 (Amasham Pharmacia Biotech Co., a plasmid for expression of a fusion protein with GST). With this vector, *Escherichia coli* (JM109) was transformed to obtain a transformed strain for expression. The transformed strain was derived according to the method disclosed in Japanese Patent Application Laid-Open No. 2003-011312. The procedure is described in detail in that patent application.

The transformed strain was pre-cultivated overnight in 10 mL of an LB-Amp culture medium. A 0.1 mL portion of the pre-culture medium was transferred to 10 mL of another LB-Amp culture medium and was cultivated at 37° C. by shaking at 170 rpm for 3 hours. Then IPTG was added thereto (final concentration: 1 mmol/L) and the cultivation was continued for 4 to 12 hours.

The bacterial strain was collected by centrifugation (78 km/s$^2$ (=8,000×g), 2 minutes, 4° C.), and was suspended again in a 1/10 quantity of phosphate buffered physiological saline at 4° C. (PBS: 8 g NaCl; 1.44 g Na$_2$HPO$_4$; 0.24 g KH$_2$PO$_4$; 0.2 g KCl; 1,000 mL purified water). The bacterial mass was crushed by freezing-thawing and sonification. Solid contaminant was eliminated by centrifugation (78 km/s$^2$ (=8,000×g), 10 minutes, 4° C.). The presence of the objective expression protein was confirmed by SDS-PAGE, and then the induced and expressed GST fusion protein was purified by use of glutathione-Sepharose 4B (Amasham Pharmacia Biotech Co.). The glutathione-Sepharose was washed with the same amount of PBS for three times (78 km/s$^2$ (=8,000×g), 1 minute, 4° C.). Thereto the same amount of PBS containing 4% bovin serum albumin was added, and the mixture was treated at 4° C. for one hour. After the treatment, it is washed with the same amount of PBS twice, and was suspended again in half an amount of PBS. A 40 µL portion of this glutathione-Sepharose was added to 1 mL of liquid extract containing no cell. The mixture was stirred gently at 4° C. to adsorb the fusion protein onto the glutathione-Sepharose. After the adsorption, the glutathione-Sepharose was recovered by centrifugation (78 km/s$^2$ (=8,000×g), 1 minute, 4° C.), and washed three times with 400 µL portions of PBS. Thereto 40 µL of 10 mmol/L glutathione was added. The mixture was stirred at 4° C. for one hour to elute the fused protein, and centrifuged (78 km/s$^2$ (=8,000×g), 2 minutes, 4° C.) to recover the supernatant liquid. The recovered supernatant liquid was dialyzed against PBS to purify the GST fused protein. The purified protein was confirmed to exhibit a single band in SDS-PAGE.

A 500 µg portion of this GST fused protein was digested by PreScission protease (Amasham Pharmacia Biotech Co., 5U). Then the protease and the GST were eliminated by passing through glutathione-Sepharose. The flow-through fraction was further introduced to a Sephadex G200 column having been equilibrated with PBS to obtain a final purified product of PHA-synthesizing enzyme. The obtained enzyme was concentrated by use of a concentrating agent (Mizubutorikun AB-1100; Atoh K.K.) for a biological sample solution to obtain a purified enzyme solution of 10 U/mL.

Reference Example 2

Production of PHA-Synthesizing Enzyme: 2

A P91 strain, an H45 strain, a YN2 strain, or a P161 strain was inoculated into 200 mL of an M9 culture medium containing 0.5% of yeast extract (Difco Co.) and 0.1% of octanoic acid, and was cultivated at 30° C. by shaking at 125 strokes/min. After 24 hour of the cultivation, the bacterial mass was recovered by centrifugation (98 km/s$^2$ (=10,000×g), 4° C., 10 minutes). The recovered mass was suspended again in 200 mL of 0.1 mol/L tris-HCl buffer (pH 8.0) and centrifuged again for washing. The bacterial mass was suspended again in 2.0 mL of 0.1 mol/L tris-HCl buffer (ph 8.0), and crushed by ultrasonic crusher. The crushed mixture was centrifuged (118 km/s$^2$ (=12,000×g), 4° C., 10 minutes), and the supernatant liquid was recovered to obtain a crude enzyme.

Further to the obtained crude enzyme, Raiho gel was added and concentrated by ultrafiltration to obtain a crude enzyme solution of 10 U/mL.

Reference Example 3

Production of PHB-Synthesizing Enzyme

A KK01 strain, a TB64 strain, or a TL2 strain was cultivated at 30° C. for 24 hours in 10 liters of an M9 culture medium (composition shown below) containing 0.5% of a yeast extract, 0.3% of a mineral solution (composition shown below). The recovered liquid culture medium was centrifuged (78 km/s$^2$ (=8,000×g), 4° C., 10 minutes). The supernatant liquid was removed, and the bacterial mass pellet was suspended again in 500 mL of a PBS solution at 4° C. This bacterial suspension were introduced in 40 mL portions successively into vessels kept cooled at 4° C., and the bacterial cells were crushed by pressurization at 216 MPa (=2,200 kg/cm$^2$) with a French press and gradual releasing through a nozzle. The resulting crushed cell liquid suspension was centrifuged at 4° C. at 78 kg/s$^2$ (=8,000×g) for 10 minutes to recover the supernatant liquid. This supernatant liquid was filtered through a filter of 0.45 µm to eliminate a solid contaminant to obtain a crude enzyme.

The above crude enzyme was concentrated with Raiho Gel by ultrafiltration to obtain a crude enzyme solution of 10 U/mL.

(M9 Culture Medium)

Na$_2$HPO$_4$ 6.2 g; KH$_2$PO$_4$ 3.0 g; NaCl 0.5 g; NH$_4$Cl 1.0 g (in one liter of culture medium, pH 7.0)

(Mineral Solution)

Nitrilotriacetic acid 1.5 g; MgSO$_4$ 3.0 g; MnSO$_4$ 0.5 g; NaCl 1.0 g; FeSO$_4$ 0.1 g; CaCl$_2$ 0.1 g; CoCl$_2$ 0.1 g; ZnSO$_4$ 0.1 g; CuSO$_4$ 0.1 g; AlK(SO$_4$)$_2$ 0.1 g; H$_3$BO$_3$ 0.1 g; Na$_2$MoO$_4$ 0.1 g; NiCl$_2$ 0.1 g (in one liter of culture medium, pH 7.0)

Example 1

In this Example, a PHA pattern was formed according to the present invention.

To 10 mL of a 0.1 mol/L phosphate buffer solution (pH 7.0), were added and mixed 2 mL of the PHA-synthesizing enzyme (10 U/mL) derived from the transformed strain in Reference Example 1, 8 g of (R)-3-hydroxyoctanoyl CoA (prepared by the method described in Eur. J. Biochem., 250, 432-439 (1997)), 0.1 g of bovin serum albumin (Sigma Co.). The mixture was immediately cooled to 4° C. This solution had a surface tension within the range of 3 to 5 mN/m (=30 to 50 dyn/cm) and a viscosity within the range of 2 to 3 mPa·s (cps).

A glass substrate of 30 mm×30 mm, 1 mm thick was washed with distilled water and dried, and then sterilized by a UV lamp.

An ink cartridge of a bubble jet printer (Trade Name: BJC-620, Canon K.K., a thermal inkjet type of inkjet printer) was washed with a 0.1 mol/L phosphate buffer solution (pH 7.0). This cartridge was filled with the above-prepared solution, and was set to the bubble jet head of the printer. The printer was placed in a thermo-hygrostat of 4° C. and 90% humidity. The glass substrate was set onto the printer. The solution was ejected in a wave line on the glass substrate. The pattern drawing was controlled by a personal computer connected to the printer. Incidentally, the employed bubble jet printer had been modified for printing on a flat plate. The amount of the ejected solution in one ejection was about 20 pL, and the breadth of the drawn line was about 80 µm.

Immediately after the ejection operation, the glass plate was brought into a thermo-hygrostat kept at 30° C. and 90% humidity and was left standing for 24 hours to synthesize a PHA.

The substrate was dried at room temperature, and washed with distilled water. The washing water remaining on the substrate surface was removed by a spin drier. The substrate was again dried at room temperature.

As described above, a PHA pattern was formed prepared on a glass substrate.

For observation of the PHA pattern formed on the substrate surface, 50 µL of an aqueous 1% Nile Blue A solution was applied to the substrate surface, and a cover glass was put thereon. The pattern was observed by a fluorescence microscope (330 to 380 nm excitation filter, 420 nm long-path absorption filter; Nikon K.K.). Thereby the pattern was confirmed to be formed as designed with a line breadth of about 70 µm. By observation with a higher magnifying power, particles of several micrometers in size were observed to be deposited in layers on the pattern face.

Another substrate having the pattern formed thereon was placed in a drier kept at 60° C. for one hour, and washed with distilled water. The washing water remaining on the substrate surface was removed by a spin drier. The substrate was again dried at 60° C. for one hour.

This substrate was dyed with an aqueous 1% Nile Blue A solution, and was observed by a fluorescence microscope in the same manner as above. Thereby it was confirmed that the PHA particles on the pattern face were fusion-bonded to form an integrated coating film.

The film thickness of the PHA pattern on the substrate was found to be about 1.2 µm in average by measurement with an optical interference type film thickness tester (K-MAC Co.).

The above-prepared solution was applied onto the formed pattern on this substrate, and a PHA was synthesized in the same manner. The substrate was dried at 60° C. for one hour, and washed with distilled water. The washing water remaining on the substrate surface was removed by a spin drier. The substrate was again dried at 60° C. for one hour.

After the drying, the above operation was repeated additionally eight times to form the PHA pattern in ten layers in total on the glass substrate.

This substrate was dyed with the aqueous 1% Nile Blue A solution, and observed by fluorescence microscope in the same manner as above. The pattern was confirmed to be formed as designed with a line breadth of about 90 µm.

The film thickness of the PHA pattern on the substrate was found to be about 10.3 µm in average by measurement with an optical interference type film thickness tester in the same manner as above.

Further, still another substrate having the pattern formed thereon was immersed into chloroform in a closed vessel, and shaken at 35° C. for 20 hours to extract the PHA from the substrate. The extract solution was filtered through a membrane filter of pore diameter of 0.45 µm, and was concentrated under a reduced pressure by a rotary evaporator. The concentrate was treated for methanolysis in a conventional manner. The methanolysis product was analyzed by a gas chromatography-mass spectrometer (GC-MS, Shimadzu QP-5050, EI method) to identify the methyl-esterified PHA monomer unit. Thereby the PHA was confirmed to be comprised of 3-hydroxyoctanoic acid units.

The molecular weight of the PHA was evaluated by gel permeation chromatography (GPC, Tosoh HLC-8020; column, Polymer Laboratory PLgel MIXED-C (5 µm); Solvent, chloroform; column temperature 40° C.; standard, polystyrene), and found that Mn was 25,000.

As described above, a fine pattern of PHA could be formed simply as designed by use of a thermal inkjet type inkjet printer.

The film thickness of the PHA coating film of the pattern face could be controlled by superposing the PHA repeatedly on the same pattern face.

Example 2

A PHA pattern was prepared by a PHA-synthesizing enzyme derived from another bacterium strain.

To 10 mL of a 0.1 mol/L phosphate buffer solution (pH 7.0), were added and mixed 2 mL of the PHA-synthesizing enzyme (10 U/mL) derived from the YN2 strain in Reference Example 2, 8 g of (R)-3-hydroxyoctanoyl CoA (prepared by the method described in Eur. J. Biochem., 250, 432-439 (1997)), and 0.1 g of bovin serum albumin (Sigma Co.). The mixture was immediately cooled to 4° C.

Solutions were prepared in the same manner as above with the PHA-synthesizing enzymes (10 U/mL) respectively prepared from the P91 strain, the H45 strain, and the P161 strain in Reference Example 2. The solutions were cooled to 4° C.

These solutions had a surface tension within the range of 3 to 5 mN/m (=30 to 50 dyn/cm) and a viscosity within the range of 2 to 3 mPa·s (cps).

The respective solutions were ejected in a wave line shape on a glass substrate by a bubble jet printer in the same manner as in Example 1. The amount of the ejected solution in one ejection was about 20 pL, and the breadth of the drawn line was about 80 µm.

After the ejection operation, each of the glass plates was brought into a thermo-hygrostat kept at 30° C. and 90% humidity and was left standing for 24 hours to synthesize PHA.

The substrates were dried at room temperature, and washed with distilled water. The washing water remaining on the substrate surfaces was removed by a spin drier. The substrates were again dried at room temperature.

As described above, PHA patterns were prepared on the glass substrates.

For observation of the PHA patterns formed on the substrate surfaces, the substrates were dyed with the aqueous 1% Nile Blue A solution, and observed by fluorescence microscopy in the same manner as in Example 1. The patterns were confirmed to be formed as designed with a line breadth of about 70 µm.

Separate substrates on which the respective patterns were formed were treated for extraction of the PHA. The extracted PHAs were analyzed by a gas chromatography-mass spectrometer (GC-MS, Shimadzu QP-5050, EI method) to identify the methyl-esterified PHA monomer unit. Thereby the PHAs were respectively confirmed to be comprised of 3-hydroxyoctanoic acid units.

The molecular weights of the PHAs were evaluated by gel permeation chromatography in the same manner as in Example 1, and found that the PHAs had Mn within the range from 22,000 to 28,000.

Even by use of the PHA-synthesizing enzyme derived from a different bacterium strain, a fine pattern of PHA could be similarly obtained according to the method of the present invention.

Example 3

In this Example, PHA patterns were prepared by PHB-synthesizing enzymes derived from different bacterium strains.

To 10 mL of a 0.1 mol/L phosphate buffer solution (pH 7.0), were added and mixed 2 mL of the PHB-synthesizing enzyme (10 U/mL) derived from KK01 strain in Reference Example 3, 8 g of (R)-3-hydroxybutyryl CoA (Sigma Co.), and 0.1 g of bovin serum albumin (Sigma Co.). The mixture was immediately cooled to 4° C.

Separately, solutions of PHB-synthesizing enzymes from a TB64 strain, and a TL2 strain were respectively prepared in the same manner, and cooled to 4° C.

These solutions had a surface tension within the range of 3 to 5 mN/m (=30 to 50 dyn/cm) and a viscosity within the range of 2 to 3 mPa·s (cps).

The respective solutions were ejected in a wave line shape on glass substrates by a bubble jet printer in the same manner as in Example 1. The amount of the ejected solution in one ejection was about 20 pL, and the breadth of the drawn line was about 80 µm.

After the ejection operation, the glass substrates were brought into a thermo-hygrostat kept at 30° C. and 90% humidity, and were left standing for 24 hours to synthesize PHA.

The substrates were dried at room temperature, and washed with distilled water. The washing water remaining on the substrate surfaces was removed by a spin drier. The substrates were again dried at room temperature.

As described above, PHA patterns were prepared on the glass substrates.

For observation of the PHA patterns formed on the substrate surfaces, the substrates were dyed with the aqueous 1% Nile Blue A solution, and observed by fluorescence microscopy in the same manner as in Example 1. The pattern was confirmed to be formed as designed with a line breadth of about 70 µm.

Other substrates on which the respective patterns were formed were treated for extraction of the PHA. The extracted PHAs were analyzed by a gas chromatography-mass spectrometer (GC-MS, Shimadzu QP-5050, EI method) to identify the methyl-esterified PHA monomer unit. Thereby the PHAs were respectively confirmed to be a PHB comprised of 3-hydroxybutyric acid units.

The molecular weight of the PHB was evaluated by gel permeation chromatography in the same manner as in Example 1, and it was found that the Mn was 69,000.

As described above, a fine pattern of PHB could be formed according to the present invention.

Even by use of the PHB-synthesizing enzyme derived from a different bacterium strains, a fine pattern of PHB could be similarly obtained according to the method of the present invention.

Example 4

In this Example, a PHA pattern was prepared by means of a piezo inkjet type printer.

In the same manner as in Example 1, to 10 mL of a 0.1 mol/L phosphate buffer solution, were added and mixed 2 mL of the PHA-synthesizing enzyme solution (10 U/mL), 8 g of (R)-3-hydroxyoctanoyl CoA, and 0.1 g of bovin serum albumin. The solution was immediately cooled to 4° C. This solution had a surface tension within the range of 3 to 5 mN/m (=30 to 50 dyn/cm) and a viscosity within the range of 2 to 3 mPa·s (cps).

An ink cartridge of a piezo inkjet type of inkjet printer (Trade Name: PM-900C, Seiko-Epson K.K.) was washed with a 0.1 mol/L phosphate buffer solution (pH 7.0). This cartridge was filled with the above-prepared solution, and was set to the inkjet head of the printer. The printer was placed in a thermo-hygrostat of a temperature of 4° C. and humidity 90%. A plain paper sheet having been sterilized by UV irradiation was set onto the printer. The solution was ejected thereon in a wave line. The drawing of the pattern was controlled by a personal computer connected to the printer. The amount of ejection of the solution in one ejection was about 25 pL, and the breadth of the drawn line was about 100 µm.

After the ejection operation, the paper sheet onto which the solution was deposited was placed in a thermo-hygrostat kept at 30° C. and 90% humidity, and was left standing for 24 hours to synthesize PHA. Then the paper sheet was dried at 60° C. for one hour.

As described above, a PHA pattern was prepared on a paper sheet.

For observation of the PHA patterns formed on the paper sheet, the portion of the sheet was dyed with the aqueous 1% Nile Blue A solution, and observed by fluorescence microscopy in the same manner as in Example 1. The pattern was confirmed to be formed as designed with a line breadth of about 90 µm.

Another paper sheet on which the pattern was formed in the same manner was treated for extraction of PHA. The extracted PHA was analyzed by a gas chromatography-mass spectrometer to identify the methyl-esterified PHA monomer unit. Thereby the PHA was confirmed to be a PHA comprised of 3-hydroxyoctanoic acid units.

The molecular weight of the PHA was evaluated by gel permeation chromatography in the same manner as in Example 1. The PHA had an Mn of 28,000.

As described above, even by use of piezo inkjet type inkjet printer, a fine pattern of PHA could be formed according to the present invention. Onto a paper sheet also, a PHA pattern could be formed.

Example 5

In this Example, a PHA pattern was formed by applying separately a PHA-synthesizing enzyme and a 3-hydroxyacyl CoA.

Four solutions were prepared. Solution-1 was prepared by adding and mixing 2 mL of the solution of a PHA-synthesizing enzyme (10 U/mL) derived from the transformed strain in Reference Example 1 to 10 mL of a 0.1 mol/L phosphate buffer solution (pH 7.0). Solution-2 was prepared by adding and mixing 8 g of (R)-3-hydroxyoctanoyl CoA (prepared by the method described in Eur. J. Biochem., 250, 432-439 (1997)), and 0.1 g of bovin serum albumin (Sigma Co.) to 10 mL of a 0.1 mol/L phosphate buffer solution (pH 7.0). Solution-3 was prepared by adding and mixing 8 g of (R)-3-hydroxy-5-phenylvaleryl CoA, and 0.1 g of bovin albumin (Sigma Co.) to 10 mL of a 0.1 mol/L phosphate buffer solution (pH 7.0). Here, the (R)-3-hydroxy-5-phenylvaleryl CoA was prepared by preparing 3-hydroxyphenylveleric acid ester by Reformatsky reaction, hydrolyzing the ester to obtain 3-hydroxy-5-phenylvaleric acid, and preparing therefrom the intended CoA derivative by the method described in Eur. J. Biochem., 250, 432-439 (1997). Solution-4 was prepared by adding and mixing 8 g of (R,S)-3-hydroxy-5-phenoxylvaleryl CoA, and 0.1 g of bovin albumin (Sigma Co.) to 10 mL of a 0.1 mol/L phosphate buffer solution (pH 7.0). Here, the (R,S)-3-hydroxy-5-phenoxylvaleryl CoA was prepared by preparing 3-hydroxy-5-phenoxylveleric acid ester by Reformatsky reaction from 3-phenoxypropanal and ethyl bromoacetate, hydrolyzing the ester to obtain 3-hydroxy-5-phenoxylvaleric acid, and preparing therefrom the intended CoA derivative by the method described in Eur. J. Biochem., 250, 432-439 (1997). The solutions were filtered with a sterilized filter of 0.22 μm and stored at room temperature. The solutions were used within 24 hours after the preparation. The four solutions had a surface tension within the range of 3 to 5 mN/m (=30 to 50 dyn/cm), and a viscosity within the range of 1 to 3 mPa·s (cps).

Four ink cartridges of the bubble jet printer employed in Example 1 were washed with a 0.1 mol/L phosphate buffer solution (pH 7.0), and were filled with the prepared four solutions respectively. The cartridges were set to the bubble jet head of the printer. This printer was placed in a thermo-hygrostat kept at 30° C. and 90% humidity. Glass substrates prepared in the same manner as Example 1 were set. Thereon, three Solutions-2, 3, and 4 were ejected in a wave line.

Then, Solution-1 was applied onto the patterns drawn by Solutions-2, 3, and 4 to mix Solution-2 and solution-1; Solution-3 and Solution-1; and Solution-4 and Solution-1.

The amount of the ejected solution in one ejection was about 20 pL, and the breadth of the drawn line was about 80 μm.

After the ejection-mixing, the mixtures were left standing to allow the PHA synthesis to proceed.

The substrates were dried at 60° C. for one hour, and washed with distilled water. The washing water remaining on the substrate surfaces was removed by a spin drier. The substrates were again dried at 60° C. for one hour.

As described above, PHA patterns were prepared on the glass substrates.

For observation of the PHA patterns formed on the substrates, the substrates were dyed with the aqueous 1% Nile Blue A solution, and observed by fluorescence microscopy in the same manner as in Example 1. The pattern was confirmed to be formed on each of the substrates as designed.

Separate substrates on which the respective patterns were formed in the same manner as above were treated for extraction of PHA in the same manner as in Example 1. The extracted PHAs were analyzed by a gas chromatography-mass spectrometer to identify the methyl-esterified PHA monomer unit. Thereby it was confirmed that the PHA of the pattern formed by Solutin-2 and Solution-1 was a PHA comprised of 3-hydroxyoctanoic units; the PHA of the pattern formed by Solutin-3 and Solution-1 was a PHA comprised of 3-hydroxyphenylvaleric acid units; and the PHA of the pattern formed by Solutin-4 and Solution-1 was a PHA comprised of 3-hydroxyphenoxyvaleric acid units.

The molecular weights of the PHAs were evaluated by gel permeation chromatography in the same manner as in Example 1. The PHA comprised of 3-hydroxyoctanoic acid units had an Mn of 25,000; the PHA comprised of 3-hydroxyphenylvaleric acid units had an Mn of 72,000; and the PHA comprised of 3-hydroxyphenoxyvaleric acid units had an Mn of 46,000.

As described above, it was confirmed that, by using different kinds of 3-hydroxyacyl CoAs, PHA patterns having different monomer unit compositions can be formed on one and the same substrate.

It was also confirmed that a PHA pattern can be formed at room temperature by applying separately a solution of a PHA-synthesizing enzyme and a solution of 3-hyroxyacyl CoA.

Example 6

In this Example, a matrix was formed by the pattern formation process of the present invention.

To 10 mL of a 0.1 mol/L phosphate buffer solution (pH 7.0), were added and mixed 2 mL of the solution of a PHA-synthesizing enzyme (10 U/mL) derived from transformed strain in Reference Example 1, 8 g of (R)-3-hydroxy-5-phenylvaleryl CoA, 0.1 g of bovin albumin (Sigma Co.), and 1 mL of an aqueous black ink (C.I. Food Black 2). Here, the (R)-3-hydroxy-5-phenylvaleryl CoA was prepared by preparing 3-hydroxyphenylveleric acid ester by Reformatsky reaction, hydrolyzing the ester to obtain 3-hydroxy-5-phenylvaleric acid, and preparing therefrom the intended CoA derivative by the method described in Eur. J. Biochem., 250, 432-439 (1997). The mixture was cooled immediately to 4° C.

This solution had a surface tension within the range of 3 to 5 mN/m (=30 to 50 dyn/cm), and a viscosity within the range of 1 to 3 mPa·s (cps).

The above solution was ejected onto a glass substrate in a grid pattern with vertical and lateral line intervals of 240

μm by a bubble jet printer in the same manner as in Example 1. The amount of the ejected solution in one ejection was about 20 pL, and the breadth of the drawn line was about 80 μm.

After the ejection operation, the glass substrate was brought into a thermo-hygrostat kept at 30° C. and 90% humidity, and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

After the drying, the above-prepared solution was again applied onto the same pattern on the same glass substrate, the PHA was synthesized, and the substrate was dried and washed in the same manner.

After the drying, the above operation was repeated additionally five times to form the PHA pattern in layers.

The PHA pattern formed on the substrate surface was observed by optical microscopy. It was found that the black matrix was formed as designed with a line breadth of about 70 μm. The substrate was dyed with an aqueous Nile Blue A solution in the same manner as in Example 1, and was observed by fluorescence microscopy. Thereby the matrix portion was found to emit fluorescence.

From another substrate having a pattern formed thereon in the same manner, the PHA was extracted. The extract was analyzed by a gas chromatography-mass spectrometer to identify the methyl-esterified PHA monomer unit in the same manner as in Example 1. Thereby the PHA was confirmed to be comprised of 3-hydroxyphenylvaleric acid units.

The molecular weight of the PHA was evaluated by gel permeation chromatography in the same manner as in Example 1. The Mn was 74,000.

On still another substrate having the pattern formed thereon in the same manner as above, an aqueous 10 μmol/L Rhodamin B solution was ejected into alternate wells of the matrix in portions of about 60 pL per well by means of a bubble jet printer (Trade name: BJC-620, Canon K.K.). The positional precision of the ejection position was ±2.5 μm.

By observation with fluorescence microscopy, the fluorescence was detected in the alternate wells, and no fluorescence was detected in the adjacent grids and on the grid.

As described above, it was confirmed that a matrix can be formed by the process of the present invention, and that the wells can hold respectively an aqueous solution.

Example 7

In this Example, a DNA array was prepared by placing a DNA probe in a matrix formed according to the present invention.

To 10 mL of a 0.1 mol/L phosphate buffer solution (pH 7.0), were added and mixed 2 mL of the solution of a PHA-synthesizing enzyme (10 U/mL) derived from the transformed strain in Reference Example 1, 8 g of (R,S)-3-hydroxy-7,8-epoxyoctanoyl CoA, and 0.1 g of bovin albumin (Sigma Co.). Here, the (R,S)-3-hydroxy-7,8-epoxyoctanyl CoA was prepared by synthesizing firstly 3-hydroxy-7-octenoic acid according to the method described in Int. J. Biol. Macromol., 12, 85-91 (1990), epoxidizing the unsaturated portion by 3-chloroperbenzoic acid, and preparing therefrom the intended derivative by the method described in Eur. J. Biochem., 250, 432-439 (1997). The mixture was cooled immediately to 4° C.

This solution had a surface tension within the range of 3 to 5 mN/m (=30 to 50 dyn/cm), and a viscosity within the range of 2 to 3 mPa·s (cps).

The above solution was ejected onto a glass substrate treated in the same manner as in Example 1 in a region of 10 mm×10 mm by the same bubble jet printer.

After the ejection operation, immediately the glass substrate was brought into a thermo-hygrostat kept at 30° C. and 90% humidity, and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

After the drying, the above-prepared solution was again applied onto the same region on the same substrate, the PHA was synthesized, and the substrate was dried and washed in the same manner.

After the drying, the above operation was repeated additionally three times to form a PHA coating film.

This substrate was immersed into chloroform in a closed vessel, and shaken at 35° C. for 20 hours to extract the PHA from the substrate. The extract solution was filtered through a membrane filter of pore diameter of 0.45 μm, and the PHA was recovered by vacuum drying. The recovered PHA was subjected to $^1$H-NMR analysis in the same manner as in Example 1. Thereby the PHA was confirmed to be comprised of 3-hydroxy-7,8-epoxyoctanoic acid units.

The molecular weight of the PHA was evaluated by gel permeation chromatography in the same manner as in Example 1. The Mn was 27,000.

Onto the PHA pattern formed on another glass substrate in the same manner as above, the ejection solution prepared in Example 6 was ejected in a grid pattern with vertical and lateral line intervals of 240 μm in the same manner as in Example 6. The amount of the ejected solution in one ejection was about 20 pL, and the breadth of the drawn line was about 80 μm.

After the ejection operation, immediately the glass substrate was brought into a thermo-hygrostat kept at 30° C. and 90% humidity, and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

After the drying, the above-prepared solution was again applied onto the same pattern on the same substrate, the PHA was synthesized, and the substrate was dried and washed in the same manner.

After the drying, the above operation was repeated additionally five times to form the PHA pattern.

The PHA pattern formed on the substrate surface was observed by optical microscopy. It was found that the black matrix pattern was drawn as designed with a line breadth of about 70 μm.

As described above, a matrix could be formed which had wells having bottoms comprised of a PHA having an epoxy group.

Next, as a DNA probe, an oligomer (18-mer) (produced by Nippon Flour Mills Co.) was prepared:

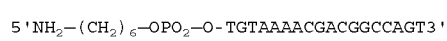

having an amino group through a phosphate group and a hexamethylene group at the hydroxyl group of 5' terminal of an oligonucleotide SEQ ID NO:1.

Separately a single-stranded DNA was synthesized which is completely complementary to the above DNA probe.

The DNA probe and the single-stranded DNA were dissolved in a TE solution containing 50 mmol/L of NaCl (pH 8) at a final concentration of 100 µmol/L. The solution was cooled from 90° C. to 25° C. in two hours to form a hybrid of the DNA probe and the single-stranded nucleic acid. This hybrid was added to an aqueous solution containing 7.5% of glycerin, 7.5% of urea, 7.5% of thiodiglycol, and 1% of acetylene alcohol at the final hybrid concentration of 8 µmol/L.

This solution had a surface tension within the range of 3 to 5 mN/m (=30 to 50 dyn/cm), and a viscosity within the range of 2 to 3 mPa·s (cps).

The hybrid solution was put into alternate wells of the matrix in portions of about 60 pL per well by means of a bubble jet printer (Trade name: BJC-620, Canon K.K.). The positional precision of the ejection was ±2.5 µm.

This substrate was placed in a thermo-hygrostat kept at 25° C. and 90% humidity for 12 hours to allow the amino group of the probe and the epoxy group on the bottom of the wells to react with each other. Then the substrate was washed with water at 80° C. to dissociate and remove, from the probe, the complementary strand forming a hybrid with the probe. Then the substrate was treated with an aqueous 1% ethanolamine solution at room temperature for one hour. By this treatment, the unreacted epoxy groups in the wells are opened to form hydroxyl groups to make the well bottoms hydrophilic. Finally, the substrate was washed with pure water, and remaining washing water on the surface was removed by a spin drier. Thus the DNA probe was immobilized on the wells.

The single-stranded DNA which was completely complimentary to this DNA probe is dissolved in a TE solution containing 50 mmol/L of NaCl (pH 8) at a final concentration of 10 µmol/L. To this solution, the glass substrate was immersed, and a hybridization reaction was allowed to proceed by cooling the solution from 80° C. to 25° C. in two hours. Then the substrate was washed with the TE buffer solution containing 10 mmol/L of NaCl (pH 8). The washing solution remaining on the substrate surface was removed by a spin drier.

Separately, 2-methyl-4,6-bis(4-N,N-dimethylaminophenyl)pyrylium iodide which fluoresces on intercalation into a two-stranded nucleic acid was dissolved in a TE solution containing 50 mmol/L of NaCl (pH 8) at a final concentration of 10 µmol/L.

This solution was introduced to all the wells on the substrate in portions of about 60 pL per well by means of a bubble jet printer (Trade name: BJC-620, Canon K.K.). The substrate was left standing for five minutes in a thermo-hygrostat of 90% humidity. Then the substrate was examined by fluorescence microscopy. Only the wells which were immobilizing the DNA probe fluoresced.

As described above, a DNA probe can be immobilized in a matrix pattern prepared by the present invention.

Example 8

Preparation of Protein Array

In this Example, a protein was immobilized in a matrix prepared according to the present invention.

A GFP solution was prepared by dissolving 1 g of GFP (Cosmo Bio Co., a green-fluorescent protein) in 100 mL of a phosphate buffer solution (pH 7.4).

A substrate on which wells had been formed in the same manner as in Example 7 was immersed in this GFP solution at 25° C. for 12 hours to cause reaction of the amino acid of the GFP surface with the epoxy group on the bottom surface to immobilize the GFP to the well.

This substrate was taken out from the solution, and was dehydrated by a pin drier. The substrate was treated with an aqueous 1% ethanolamine solution at room temperature for one hour to open the unreacted epoxy rings in the wells. Then the substrate was washed with pure water and dried. By this treatment, the epoxy rings which did not react with the GFP in the well are opened to form hydroxyl groups. Thereby the bottoms of the wells were made more hydrophilic.

By observation of this substrate by fluorescence microscopy, fluorescence of GFP was detected in all wells, and no fluorescence was detected on the grid.

As shown above, the matrix pattern prepared according to the present invention can immobilize a protein.

Example 9

In this Example, wells were formed by employing a PHA-decomposing enzyme.

Two solutions were prepared. Solution-5 was prepared by adding and mixing 2 mL of the solution of a PHA-synthesizing enzyme (10 U/mL) derived from the transformed strain in Reference Example 1, and 8 g of (R)-3-hydroxypimelyl CoA, and 0.1 g of bovin albumin (Sigma Co.) to 10 mL of a 0.1 mol/L phosphate buffer solution (pH 7.0). Here the (R)-3-hydroxypimelyl CoA was prepared according to the method described in J. Bacteriol., 182, 2753-2760 (2000). Solution-6 was prepared by adding and mixing 2 mL of the same PHA-synthesizing enzyme solution (10 U/mL), 8 g of (R)-3-hydroxyoctanoyl CoA, and 0.1 g of bovin serum albumin (Sigma Co.) to 10 mL of a 0.1 mol/L phosphate buffer solution (pH 7.0). Here, the (R)-3-hydroxyoctanoyl CoA was prepared according to the method described in Eur. J. Biochem., 250, 432-439 (1997). The solutions were immediately cooled to 4° C.

These solutions had a surface tension within the range of 3 to 5 mN/m (=30 to 50 dyn/cm), and a viscosity within the range of 2 to 3 mPa·s (cps).

The above Solution-5 was ejected onto a glass substrate in a rectangular region of 300 µm×3,000 µm by a bubble jet printer in the same manner as in Example 1.

Immediately after the ejection operation, the glass substrate was brought into a thermo-hygrostat kept at 30° C. and 90% humidity, and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

After the drying, the above Solution-5 was again applied onto the same region on the same substrate to synthesize the PHA, and the substrate was dried and washed in the same manner. After the drying, the above operation was repeated additionally five times to synthesize PHA.

Further, Solution-6 was applied onto the same region on the same substrate, the PHA was synthesized, and the substrate was dried and washed in the same manner. The above operation was repeated additionally two times.

A PHA coating film was prepared as above.

The mass of the PHA of the PHA coating film was measured by a time-of-flight secondary ion mass spectrometer (TOF-SIMS IV; CAMECA Co.). The obtained mass spectrum showed that the surface of the PHA pattern was constructed from a homopolymer comprised of 3-hydroxyoctanoic acid units. The surface of the pattern was scraped little by little by ion sputtering with measurement of the PHA film thickness by an optical interference type thickness tester and with measurement of mass spectrum by TOF-SIMS. Thereby, it was confirmed that, from the portion of the film at 7.8 μm thick from the substrate surface, the layer component was changed to a homopolymer comprised of 3-hydroxypimelic acid unit.

Next, A PHA-decomposing enzyme was obtained as below.

A YN2 strain bacteria was inoculated into 10 Sakaguchi flasks containing dispensed one liter of M9 culture medium containing 0.5% of peptone and 0.1% of octanoic acid. The cultivation was conducted at 30° C. by shaking at 125 strokes/min. After 72 hours of cultivation, the bacterial mass was recovered by centrifugation (98 km/s$^2$ (=10,000×g), 4° C., 10 minutes). The recovered bacterial mass was washed with methanol several times, and was dried by vacuum drying. From the dried bacterial mass, PHA was extracted with chloroform at 35° C. with stirring for three days. The extract solution was filtered by a filter of 0.45 μm. The filtrate was concentrated by an evaporator, and the evaporation residue was dried under vacuum to obtain about 4 g of a PHA polymer. This polymer was analyzed in the same manner as in Example 1 by a gas chromatography-mass spectrometer to identify the methyl-esterified PHA monomer unit. Thereby the PHA was confirmed to be comprised of 3-hydroxyoctanoic acid units.

An M9 culture medium containing 0.5% polypeptone and 1.2% agar was autoclaved. The culture medium was dispensed to Petri dishes for use as an agar culture medium. A 2 g portion of the above-obtained PHA was dissolved in 10 mL of acetone. This solution was added in 0.5 mL portions to the agar culture medium in the dishes, and was spread uniformly over the agar surfaces. After standing left in a draft chamber overnight, the surface of the agar became white turbid by deposition of the PHA. Onto the agar culture mediums, liquid suspensions of soils collected from outdoors were applied. The cultures were kept at 30° C. for one week for incubation. From the formed colonies which caused a clear zone on the periphery by decomposition of the PHA, bacterial strains were isolated. The isolated bacterial strains were applied on the same agar culture medium. The strain which formed largest clear zone in a shorter time was selected as the bacterial strain for obtaining the HPA-decomposing enzyme.

Separately, to 10 mL of sterilized water, 1 g of the above PHA and 0.5 mL of Tween 20 were added, and the mixture was emulsified by a blender. The resulting emulsion was added to an M9 medium containing 0.5% of polypeptone. Thereto the above isolated bacterial strain was inoculated, and cultivated at 30° C. by shaking at 125 strokes per minute. After 72 hours, the liquid culture was centrifuged (98 km/s$^2$ (=10.000×g), 4° C., 10 min.) to separate the bacterial mass and the supernatant liquid. The bacterial mass was suspended again in 200 mL of a 0.1 mol/L tris-HCl buffer solution (pH 8.0) and centrifuged again for washing. The bacterial mass was suspended again in 2 mL of a 0.1 mol/L tris-HCl buffer solution (pH 8.0) and crushed by an ultrasonic crusher. This crushed mass was centrifuged (118 km/s$^2$ (=12,000×g), 4° C., 10 min.) to recover the supernatant liquid. This supernatant liquid and the above-separated supernatant liquid were concentrated by ultrafiltration. The concentrate was suspended again in a 0.1 mol/L tris-HCl buffer solution (pH 8.0) to obtain a solution of a crude PHA-decomposing enzyme.

This solution was ejected on the above-prepared rectangular PHA coating-film by means of a bubble jet printer (Trade name: BJC-620, Canon K.K.) to form dots of about 100 μm diameter at intervals of about 200 μm in the length direction.

Thereafter immediately the substrate was placed in a thermo-hygrostat kept at 30° C. and 90% humidity, and kept standing therein for 24 hours. Then the substrate was dried at 60° C. for one hour, the surface of the substrate was washed with distilled water, and dried at 60° C. for one hour.

In this state, the thickness of the PHA film was measured by an optical interference type film thickness tester in the same manner as in Example 1. The thickness was 10.8 μm in average at the non-lipase-applied portion, and 2.8 to 6.2 μm at the lipase-applied portion. This portion was examined by measuring the mass spectrum with TOF-SIMS in the same manner as above. The portion was found to be constructed of a homopolymer comprised of 3-hyddroxypimelic acid units.

As described above, PHA wells were formed by use of a lipase. Incidentally, the PHA comprised of 3-hydroxypimelic acid units has hydroxyl groups and is hydrophilic, whereas the PHA comprised of 3-hydroxyoctanoic acid is hydrophobic.

Into the alternate wells on the substrate, an aqueous 10 μmol/L Rhodamin B solution was ejected in an amount of about 20 pL per well by means of a bubble jet printer (Trade name: BJC-620; Canon K.K.). The positional precision of the ejection was ±2.5 μm.

The substrate was observed by fluorescence microscopy. Fluorescence was detected in a circle shape of about 80 μm diameter at intervals of about 400 μm. No fluorescence was detected on the other portions.

As described above, wells can be formed by use of a PHA-decomposing enzyme.

Example 10

In this Example, a fine flow channel was formed by the pattern formation process of the present invention.

To 10 mL of a 0.1 mol/L phosphate buffer solution (pH 7.0), were added and mixed 2 mL of the solution of the PHA-synthesizing enzyme (10 U/mL) derived from the transformed strain in Reference Example 1, 8 g of (R)-3-hydroxy-5-phenylvaleryl CoA, and 0.1 g of bovin albumin (Sigma Co.). Here, the (R)-3-hydroxy-5-phenylvaleryl CoA was prepared by preparing 3-hydroxyphenylveleric acid ester by Reformatsky reaction, hydrolyzing the ester to obtain 3-hydroxy-5-phenylvaleric acid, and preparing therefrom the intended CoA derivative by the method described in Eur. J. Biochem., 250, 432-439 (1997). The mixture was cooled immediately to 4° C.

This solution had a surface tension within the range of 3 to 5 mN/m (=30 to 50 dyn/cm), and a viscosity within the range of 1 to 3 mPa·s (cps).

This solution was ejected onto a glass substrate to draw a flow channel pattern by a bubble jet printer in the same manner as in Example 1. The pattern was formed in a -shape having side length of 20 mm with the two end faces of the pattern positioned on one side edge face of the glass substrate. A similar pattern was formed 200 μm inside. The volume of the ejected solution in one ejection was about 20 pL, and the breadth of the pattern line was about 80 μm.

Immediately after the ejection operation, the glass substrate was placed in a thermo-hygrostat kept at 30° C. and 90% humidity, and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

After the drying, the above-prepared solution was again applied onto the same pattern on the same substrate, and the PHA was synthesized. The substrate was dried and washed in the same manner as above.

After the drying, the above operation was repeated additionally five times to form the PHA pattern on the substrate.

On this glass substrate, another substrate prepared in the same manner as in Example 1 was superposed with interposition of a spacer of 5 μm. This pair of the substrates were placed in a dryer at 60° C. for one hour to allow the pattern face to adhere tightly to the glass substrates.

Into the interspace between the substrates, a Nile Blue solution was introduced for dyeing, and the substrates were observed by fluorescence microscopy. Formation of two lines of about 90 μm in width were confirmed in a U-shaped pattern with an interval of about 100 μm.

To an opening of the flow channel of another pair of the substrates patterned in the same manner, a Taigon micro bore tube (S-54-HL; Saint Gobain Co.) having inside diameter of 0.25 mm and outside diameter of 0.76 mm was bonded by an elastic adhesive (EP-001; Cemedine Co.). The substrates were placed on a fluorescence microscope. Into the flow channel formed between the substrates, an aqueous 10 μmol/L Rhodamine B solution was introduced at a flow rate of 0.05 μL/hr by a syringe pump (CFV-3200; Nippon Koden K.K.) with observation by fluorescence. Thereby, the fluorescent solution was observed to flow through the flow channel. Leakage of the fluorescent solution from the flow channel was not observed.

As described above, a fine flow channel can be constructed for flow of a solution according to the present invention.

Example 11

In this Example, a PHA pattern was formed in multiple layers by the process of the present invention.

Four solutions were prepared. Solution-5 was prepared by adding and mixing 2 mL of the solution of a PHA-synthesizing enzyme (10 U/mL) derived from the transformed strain in Reference Example 1, 8 g of (R)-3-hydroxypimelyl CoA, and 0.1 g of bovin albumin (Sigma Co.) to 10 mL of a 0.1 mol/L phosphate buffer solution (pH 7.0). Here the (R)-3-hydroxypimelyl CoA was prepared according to the method described in J. Bacteriol., 182, 2753-2760 (2000). Solution-6 was prepared by adding and mixing 2 mL of the same PHA-synthesizing enzyme solution (10 U/mL), 6 g of (R)-3-hydorxypimelyl CoA, 2 g of (R)-3-hydroxy-5-phenylvaleryl CoA, and 0.1 g of bovin serum albumin (Sigma Co.) to 10 mL of a 0.1 mol/L phosphate buffer solution (pH 7.0). Here, the (R)-3-hydroxy-5-phenylvaleryl CoA was prepared by preparing 3-hydroxyphenylveleric acid ester by Reformatsky reaction, hydrolyzing the ester to obtain 3-hydroxy-5-phenylvaleric acid, and preparing therefrom the intended CoA derivative by the method described in Eur. J. Biochem., 250, 432-439 (1997). Solution-7 was prepared by adding and mixing 2 mL of the same PHA-synthesizing enzyme solution (10 U/mL), 2 g of (R)-3-hydorxypimelyl CoA, 6 g of (R)-3-hydroxy-5-phenylvaleryl CoA, and 0.1 g of bovin serum albumin (Sigma Co.) to 10 mL of a 0.1 mol/L phosphate buffer solution (pH 7.0). Solution-8 was prepared by adding and mixing 2 mL of the same PHA-synthesizing enzyme solution (10 U/mL), 8 g of (R)-3-hydroxy-5-phenylvaleryl CoA, and 0.1 g of bovin serum albumin (Sigma Co.) to 10 mL of a 0.1 mol/L phosphate buffer solution (pH 7.0). The solutions were immediately cooled to 4° C.

These solutions had a surface tension within the range of 3 to 5 mN/m (=30 to 50 dyn/cm), and a viscosity within the range of 2 to 3 mPa·s (cps).

Firstly, Solution-5 was ejected in a wave line shape on a glass substrate by a bubble jet printer in the same manner as in Example 1. The amount of the ejected solution in one ejection was about 20 pL, and the breadth of the drawn line was about 80 μm.

After the ejection operation, the glass substrate was placed in a thermo-hygrostat kept at 30° C. and 90% humidity and was left standing for 24 hours to synthesize PHA.

The substrate was dried at 60° C. for one hour, and washed with distilled water. The washing water remaining on the substrate surface was removed by a spin drier. The substrate was again dried at 60° C. for one hour.

Then, Solution-6 was applied onto the same pattern on the same substrate, the PHA was synthesized, and the substrate was dried and washed in the same manner. Solution-7, and solution-8 were successively applied in the same manner to form PHA patterns in superposition.

A PHA coating film was prepared as above.

The mass of the PHA of the pattern surface was measured by a time-of-flight secondary ion mass spectrometer (TOF-SIMS IV; CAMECA Co.). The obtained mass spectrum showed that the surface of the pattern was formed from a homopolymer comprised of 3-hydroxyphenylvaleric acid units. The surface of the pattern was scraped little by little by ion sputtering with measurement of the mass spectrum by TOF-SIMS. Thereby, layers were found to be superposed thereon successively in the order of a layer of a copolymer of 3-hydroxyphenylvaleric acid and 3-hydroxypimelic acid (molar ratio of 3:1); a layer of a copolymer of 3-hydorxyphenylvaleric acid and 3-hydroxypimelic acid (molar ratio of 1:3); and a layer of a homopolymer of 3-hydroxypimelic acid units.

A multi-layered PHA pattern can be formed according the present invention as shown above.

Example 12

In this Example, the PHA of the pattern was crosslinked by chemical modification.

To 10 mL of a 0.1 mol/L phosphate buffer solution (pH 7.0), were added and mixed 2 mL of the solution of a PHA-synthesizing enzyme (10 U/mL) derived from the transformed strain in Reference Example 1, 6 g of (R,S)-3-hydroxy-5-phenoxyvaleryl CoA, 2 g of (R,S)-3-hydroxy-7, 8-epoxyoctanoyl CoA, and 0.1 g of bovin albumin (Sigma Co.). Here, the (R,S)-3-hydroxy-5-phenoxylvaleryl CoA was prepared by preparing 3-hydroxyphenoxylveleric acid ester by Reformatsky reaction from 3-phenoxypropanal and ethyl bromoacetate, hydrolyzing the ester to obtain 3-hydroxy-5-phenoxylvaleric acid, and preparing therefrom the intended CoA derivative by the method described in Eur. J. Biochem., 250, 432-439 (1997)). The (R,S)-3-hydroxy-7,8-epoxyoctanyl CoA was prepared by synthesizing 3-hydroxy-7-octenoic acid according to the method described in Int. J. Biol. Macromol., 12, 85-91 (1990), epoxidizing the unsaturated portion by 3-chloroperbenzoic acid, and preparing therefrom the intended derivative by the method described in Eur. J. Biochem., 250, 432-439 (1997). The mixture was cooled immediately to 4° C.

This solution had a surface tension within the range of 3 to 5 mN/m (=30 to 50 dyn/cm), and a viscosity within the range of 2 to 3 mPa·s (cps).

The solution was ejected in a wave line shape on a glass substrate by a bubble jet printer in the same manner as in Example 1. The amount of the ejected solution in one ejection was about 20 pL, and the breadth of the drawn line was about 80 μm.

After the ejection operation, the glass substrate was placed in a thermo-hygrostat kept at 30° C. and 90% humidity, and was left standing for 24 hours to synthesize PHA.

The substrate was dried at room temperature, and washed with distilled water. The washing water remaining on the substrate surface was removed by a spin drier. The substrate was again dried at room temperature.

The substrate was dyed with an aqueous 1% Nile Blue A solution, and was observed by fluorescence microscopy in the same manner as in Example 1. The intended pattern was confirmed to be formed.

Another substrate patterned in the same manner was immersed in chloroform in a closed vessel, and shaken at 35° C. for 20 hours to extract the PHA from the substrate. The extract solution was filtered through a membrane filter of pore diameter of 0.45 μm. The extract solution was subjected to $^1$H-NMR analysis in the same manner as in Example 7. Thereby the PHA was confirmed to be comprised of 74% of 3-hydroxy-5-phenoxyvaleric acid and 26% of 3-hydroxy-7,8-epoxyoctanoic acid.

Another substrate patterned in the same manner was immersed in 50 mL of water. Therein 0.5 g of hexamethylenediamine was dissolved as a crosslinking agent. After confirming dissolution thereof, the water was removed by freeze drying (this substrate is referred to as Substrate A). This Substrate A was allowed to react at 70° C. for 12 hours (this substrate is referred to as Substrate B).

Substrate A and Substrate B were immersed in chloroform in a closed vessel, and shaken at 35° C. for 20 hours to extract the PHA form the substrate. The extract solution was filtered through a membrane filter of pore diameter of 0.45 μm. The chloroform was removed by vacuum drying. The remaining solid was examined by a differential scanning calorimeter (DSC; Perkin Elmer Co.; Pyris 1, temperature elevation rate: 10° C./min.). As the results, Substrate A had a sharp exothermic peak at about 90° C., which showed that crosslinking between polymers were progressing by reaction of the epoxy group of the polymer and hexamethylenediamine, whereas substrate B did not show remarkable heat flow, which signified that the crosslinking reaction had been nearly completed.

Still other substrates prepared in the same manner as above were subjected to IR absorption measurement (FT-IR; Perkin Elmer Co.; 1720X). As the results, the absorption peaks of the amine (at about 3,340 cm$^{-1}$) and epoxy (at about 822 cm$^{-1}$) were observed with Substrate A, whereas no peak was observed with Substrate B.

The PHA pattern after the crosslinking was observed by dyeing of Substrate B with an aqueous Nile Blue A solution, and by fluorescence microscopy in the same manner as in Example 1. Thereby a pattern was confirmed to be drawn with the line breadth of about 90 μm as designed.

As described above, the polymer of the PHA pattern of the present invention can be crosslinked by chemical modification.

Example 13

In this Example, a graft chain was attached to the PHA of the pattern by chemical modification.

A PHA pattern was formed on a glass substrate in the same manner as in Example 12.

This substrate was immersed in a terminal amino-modified polysiloxane (Modified Silicone Oil TSF4700; GE Toshiba Silicone K.K.), and the reaction was allowed to proceed at 70° C. for two hours. Then the substrate was washed with methanol, and was dried. Thus the PHA pattern was grafted with polysiloxane chains.

For observation of the grafted PHA pattern, Substrate B was dyed with an aqueous Nile Blue A solution. This substrate was observed by fluorescence microscopy. Thereby the pattern was confirmed to be formed as designed with the line breadth of about 90 μm.

Example 14

In this Example, a functional group of the PHA pattern formed according to the present invention was changed to another functional group by chemical modification.

To 10 mL of 0.1 mol/L phosphate buffer solution (pH 7.0), were added and mixed 2 mL of the PHA-synthesizing enzyme (10 U/mL) derived from the transformed strain in Reference Example 1, 8 g of (R,S)-3-hydroxy-ω-(4-vinylphenyl)valeryl CoA (prepared by the method described in Eur. J. Biochem., 250, 432-439 (1997)), and 0.1 g of bovin serum albumin (Sigma Co.). The mixture was immediately cooled to 4° C.

This solution had a surface tension within the range of 3 to 5 mN/m (=30 to 50 dyn/cm) and a viscosity within the range of 2 to 3 mPa·s (cps).

The solution was ejected in a wave line shape on a glass substrate by a bubble jet printer in the same manner as in Example 1. The amount of the ejected solution in one ejection was about 20 pL, and the breadth of the drawn line was about 80 μm.

Immediately after the ejection operation, the glass substrate was placed in a thermo-hygrostat kept at 30° C. and 90% humidity, and was left standing for 24 hours to synthesize PHA.

The substrate was dried at room temperature, and washed with distilled water. The washing water remaining on the substrate surface was removed by a spin drier. The substrate was again dried at room temperature.

The substrate was dyed with the aqueous 1% Nile Blue A solution, and was observed by fluorescence microscopy in the same manner as in Example 1. The intended pattern was confirmed to be formed.

The patterned substrate was immersed in chloroform in a closed vessel, and shaken at 35° C. for 20 hours to extract the PHA on the substrate. The extract solution was filtered through a membrane filter of pore diameter of 0.45 μm. The extract solution was subjected to $^1$H-NMR analysis in the same manner as in Example 1. Thereby the PHA was found to be comprised of 3-hydroxy-ω-(4-vinylphenyl)valeric acid.

Another substrate patterned in the same manner was immersed in 50 mL of hexane. Thereto a solution of 2 g m-chloroperbenzoic acid in 20 mL hexane was added dropwise. The mixed solution was stirred at 5° C. for 12 hours, and 20° C. for 12 hours to allow the reaction to proceed.

The substrate was dyed with an aqueous Nile Blue solution, and observed by fluorescence microscopy in the same manner as in Example 1. Thereby a pattern was confirmed to be formed as intended.

The mass of surface portion of the PHA modified chemically in the same manner on another substrate was measured by a time-of-flight secondary ion mass spectrometer (TOF-SIMS IV; CAMECA Co.). From the obtained mass spectrum, the surface of the pattern is estimated to be constructed of a PHA comprised of 3-hydroxy ω-(4-epoxyphenyl)valeric acid units.

As described above, a functional group of the PHA of the present invention can be changed to another functional group by chemical modification.

Example 15

In this Example, a compound was bonded to the PHA pattern formed according to the present invention by chemical modification.

To 10 mL of 0.1 mol/L phosphate buffer solution (pH 7.0), were added and mixed 2 mL of the PHA-synthesizing enzyme (10 U/mL) derived from the transformed strain in Reference Example 1, 8 g of (R,S)-3-hydroxy-8-bromooctanoyl CoA (prepared by the method described in Eur. J. Biochem., 250, 432-439 (1997)), and 0.1 g of bovin serum albumin (Sigma Co.). The mixture was immediately cooled to 4° C.

This solution had a surface tension within the range of 3 to 5 mN/m (=30 to 50 dyn/cm) and a viscosity within the range of 2 to 3 mPa·s (cps).

The solution was ejected in a wave line shape on a glass substrate by a bubble jet printer in the same manner as in Example 1. The amount of the ejected solution in one ejection was about 20 pL, and the breadth of the drawn line was about 80 μm.

Immediately after the ejection operation, the glass substrate was placed in a thermo-hygrostat kept at 30° C. and 90% humidity, and was left standing for 24 hours to synthesize PHA.

The substrate was dried at room temperature, and washed with distilled water. The washing water remaining on the substrate surface was removed by a spin drier. The substrate was again dried at room temperature.

The substrate was dyed with an aqueous 1% Nile Blue A solution, and was observed by fluorescence microscopy in the same manner as in Example 1. Thereby the intended pattern was confirmed to be formed.

Another substrate patterned in the same manner was immersed in chloroform in a closed vessel, and shaken at 35° C. for 20 hours to extract the PHA on the substrate. The extract solution was filtered through a membrane filter of pore diameter of 0.45 μm. The extract solution was subjected to $^1$H-NMR analysis in the same manner as in Example 7. Thereby the PHA was found to be comprised of 3-hydroxy-8-bromooctanoic acid.

Another substrate patterned in the same manner was immersed in 12 mL of hexane, and the atmosphere in the system was replaced with nitrogen. Thereto, by keeping the system at a room temperature, were added a solution of 825 mg sodium 2-(2'-mercaptoethyl)amido-2-methylpropane-sulfonate represented by Chemical Formula (1) in 18 mL of hexane, and 330 μL of diethylamine. The mixture was stirred gently for 24 hours to allow the reaction to proceed.

This substrate was dyed with an aqueous Nile Blue solution, and observed by fluorescence microscopy in the same manner as in Example 1. Thereby a pattern was confirmed to be formed as intended.

The mass of the PHA formed on still another substrate in the same manner was measured by a time-of-flight secondary ion mass spectrometer (TOF-SIMS IV, CAMECA Co.). From the obtained mass spectrum, the surface of the pattern is estimated to be constructed of a PHA comprised of the units represented by Chemical Formula (2).

As described above, a compound can be bonded to the PHA of the present invention.

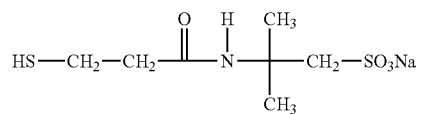

(1)

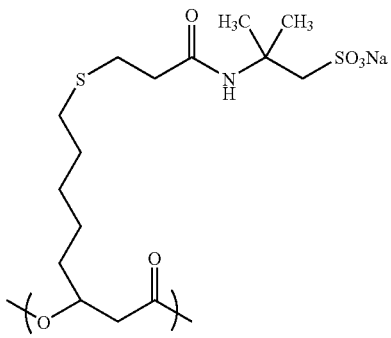

(2)

Example 16

In this Example, a compound was bonded to the PHA pattern formed according to the present invention by chemical modification.

To 10 mL of 0.1 mol/L phosphate buffer solution (pH 7.0), were added and mixed 2 mL of the PHA-synthesizing enzyme solution (10 U/mL) derived from the transformed strain in Reference Example 1, 8 g of (R)-3-hydroxypimelyl CoA, and 0.1 g of bovin albumin (Sigma Co.). Here the (R)-3-hydroxypimelyl CoA was prepared according to the method described in J. Bacteriol., 182, 2753-2760 (2000). The mixture was immediately cooled to 4° C.

This solution had a surface tension within the range of 3 to 5 mN/m (=30 to 50 dyn/cm) and a viscosity within the range of 2 to 3 mPa·s (cps).

The solution was ejected in a wave line shape on a glass substrate by a bubble jet printer in the same manner as in Example 1. The amount of the ejected solution in one ejection was about 20 pL, and the breadth of the drawn line was about 80 μm.

Immediately after the ejection operation, the glass substrate was placed in a thermo-hygrostat kept at 30° C. and 90% humidity, and was left standing for 24 hours to synthesize PHA.

The substrate was kept in a drier at 100° C. for one hour, and washed with distilled water. The washing water remaining on the substrate surface was removed by a spin drier. The substrate was dried at room temperature.

The substrate was dyed with an aqueous 1% Nile Blue A solution, and was observed by fluorescence microscopy in the same manner as in Example 1. Thereby the intended pattern was confirmed to be formed.

The patterned substrate was immersed in chloroform in a closed vessel, and shaken at 35° C. for 20 hours to extract the PHA on the substrate. The extract solution was filtered through a membrane filter of pore diameter of 0.45 μm. The extract solution was subjected to $^1$H-NMR analysis in the same manner as in Example 7. Thereby the PHA was found to be comprised of (R)-3-hydroxypimelic acid.

Separately, 547 mg of p-toluidine-2-sulfonic acid, and 100 mL of pyridine were placed in a 200-mL two-neck flask and stirred under a nitrogen atmosphere. Then another substrate having been patterned in the same manner as above was immersed in the solution in the flask. Thereto, 0.8 mL of triphenyl phosphite was added. The flask was heated at 100° C. for 6 hours. After the reaction, this substrate was dyed with an aqueous 1% Nile Blue A solution, and was observed by fluorescence microscopy in the same manner as in Example 1. Thereby the intended pattern was confirmed to be formed.

The mass of the PHA formed on still another substrate in the same manner as above was measured by a time-of-flight secondary ion mass spectrometer (TOF-SIMS IV, CAMECA Co.). From the obtained mass spectrum, the surface of the pattern is estimated to be constructed of a PHA comprised of the units represented by Chemical Formula (3) below.

As described above, a compound can be added to the PHA of the present invention.

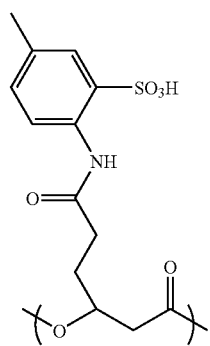

(3)

Sequence Listings Free Text

<210> 1

<223> oligonucleotide for DNA probe

This application claims priority from Japanese Patent Application No. 2004-047941 on Feb. 24, 2004, which is hereby incorporated by reference herein.

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: oligonucleotide for DNA probe

<400> SEQUENCE: 1
tgtaaaacga cggccagt					18

What is claimed is:

1. A process for forming a pattern comprised of a polyhydroxyalkanoate on a substrate, the process comprising the steps of:
    making a polyhydroxyalkanoate-synthesizing enzyme and a 3-hydroxyacyl CoA coexist with each other in an intended pattern on a substrate,
    forming the pattern comprised of the polyhydroxyalkanoate on the substrate by polymerizing the 3-hydroxyacyl CoA by action of the enzyme.

2. The process for forming a pattern according to claim 1, wherein the making step comprises a step of applying a solution containing the polyhydroxyalkanoate-synthesizing enzyme and the 3-hydroxyacyl CoA to the substrate in an intended pattern to synthesize the polyhydroxyalkanoate in the solution.

3. The process for forming a pattern according to claim 2, wherein the solution includes a first solution containing a polyhydroxyalkanoate-synthesizing enzyme and no 3-hydroxyalkanoate, and a second solution containing a 3-hydroxyalkanoate and no polyhydroxyalkanoate-synthesizing enzyme; and
    one of the first solution and the second solution is firstly applied to the substrate, and then the other solution is applied onto the firstly applied solution.

4. The process for forming a pattern according to claim 1, wherein, after the synthesizing step, the making step for coexistence and the synthesizing step are repeated.

5. The process for forming a pattern according to claim 1, wherein the process further comprises a step of drying the substrate after the synthesizing step.

6. The process for forming a pattern according to claim 1, wherein the process further comprises a step of heating the substrate up to a temperature higher than a glass transition temperature of the synthesized polyhydroxyalkanoate after the synthesizing step.

7. The process for forming a pattern according to claim 1, wherein the process further comprises a step of producing the polyhydroxyalkanoate-synthesizing enzyme by employing a microorganism having an ability to produce the enzyme.

8. The process for forming a pattern according to claim 7, wherein the microorganism is comprised of a transformant having a gene relating to the ability to produce the polyhydroxyalkanoate-synthesizing enzyme.

9. The process for forming a pattern according to claim 8, wherein the gene is derived from a microorganism having the ability to produce the polyhydroxyalkanoate-synthesizing enzyme.

10. The process for forming a pattern according to claim 8, wherein the host microorganism of the transformant is *Escherichia coli*.

11. The process for forming a pattern according to claim 9, wherein the host microorganism of the transformant is *Escherichia coli*.

* * * * *

UNITED STATES PATENT AND TRADEMARK OFFICE
CERTIFICATE OF CORRECTION

| | |
|---|---|
| PATENT NO. | : 7,358,070 B2 |
| APPLICATION NO. | : 11/062816 |
| DATED | : April 15, 2008 |
| INVENTOR(S) | : Shinya Kozaki et al. |

It is certified that error appears in the above-identified patent and that said Letters Patent is hereby corrected as shown below:

COLUMN 2:

Line 20, "increase the" should read --an increase in--.

COLUMN 3:

Line 34, "polyhyroxyalkanoate-synthesizing" should read
       --polyhydroxyalkanoate-synthesizing--.

COLUMN 4:

Line 17, "(R)-3-hydorxyacyl CoA" should read --(R)-3-hydroxyacyl CoA--.

COLUMN 5:

Line 36, "KKO1" should read --KK01--.

COLUMN 6:

Line 26, "lisozyme" should read --a lysozyme--.

COLUMN 7:

Line 2, "bovin" should read --bovine--;
  Line 8, "Reagent-4,5,5'-dithio-bis(2-" should read --Reagent-4
       5,5'-dithio-bis(2- --;
  Line 36, "3-hydrocya-" should read --3-hydroxya- --;
  Line 40, "contains" should read --contain--; and
  Line 52, "3-hydrocyacyl CoA" should read --3-hydroxyacyl CoA--.

COLUMN 10:

Line 58, "3-hydorxyacyl CoA." should read --3-hydroxyacyl CoA.--.

COLUMN 11:

Line 35, "3-hydorxyacyl CoA" should read --3-hydroxyacyl CoA--;
  Line 39, "3-hyroxyacyl CoA" should read --3-hydroxyacyl CoA--; and
  Line 41, "3-hydorxyacyl" should read --3-hydroxyacyl--.

UNITED STATES PATENT AND TRADEMARK OFFICE
CERTIFICATE OF CORRECTION

PATENT NO.       : 7,358,070 B2
APPLICATION NO.  : 11/062816
DATED            : April 15, 2008
INVENTOR(S)      : Shinya Kozaki et al.

It is certified that error appears in the above-identified patent and that said Letters Patent is hereby corrected as shown below:

COLUMN 15:

Line 55, "bovin" should read --bovine--.

COLUMN 16:

Line 27, "24 hour" should read --24 hours--; and
Line 55, "were" should read --was--.

COLUMN 17:

Line 20, "bovin" should read --bovine--.

COLUMN 18:

Line 61, "bovin" should read --bovine--.

COLUMN 19:

Line 50, "bovin" should read --bovine--.

COLUMN 20:

Line 26, "a different" should read --different--; and
Line 36, "bovin" should read --bovine--.

COLUMN 21:

Line 28, "bovin" should read --bovine--;
Line 31, "bovin" should read --bovine--;
Line 35, "nylveleric" should read --nylvaleric--;
Line 40, "bovin" should read --bovine--;
Line 44, "phenoxyveleric" should read --phenoxyvaleric--; and
Line 66, "solution-1;" should read --Solution-1;--.

UNITED STATES PATENT AND TRADEMARK OFFICE
CERTIFICATE OF CORRECTION

PATENT NO. : 7,358,070 B2
APPLICATION NO. : 11/062816
DATED : April 15, 2008
INVENTOR(S) : Shinya Kozaki et al.

It is certified that error appears in the above-identified patent and that said Letters Patent is hereby corrected as shown below:

COLUMN 22:

Line 24, "Solutin-2" should read --Solution-2--;
    Line 26, "Solutin-3" should read --Solution-3--;
    Line 28, "Solutin-4" should read --Solution-4--;
    Line 43, "3-hyroxyacyl" should read --3-hydroxyacyl--;
    Line 53, "bovin" should read --bovine--; and
    Line 56, "3-hydroxyphenylveleric" should read --3-hydroxyphenylvaleric--.

COLUMN 23:

Line 59, "bovin" should read --bovine--.

COLUMN 25:

Line 36, "compli-" should read --comple---.

COLUMN 26:

Line 32, "bovin" should read --bovine--; and
    Line 38, "bovin" should read --bovine--.

COLUMN 27:

Line 51, "largest" should read --the largest--; and
    Line 52, "HPA-" should read --PHA- --.

COLUMN 28:

Line 26, "3-hyddroxypimelic" should read --3-hydroxypimelic--;
    Line 54, "bovin" should read --bovine--; and
    Line 56, "3-hydroxyphenylveleric" should read --3-hydroxyphenylvaleric--.

COLUMN 29:

Line 1, "a-shape" should read --a shape--;
    Line 2, "side" should read --a side--;
    Line 59, "bovin" should read --bovine--;
    Line 65, "(R)-3-hydorxypimelyl CoA" should read --(R)-3-hydroxypimelyl
        CoA--; and
    Line 66, "bovin" should read --bovine--.

UNITED STATES PATENT AND TRADEMARK OFFICE
CERTIFICATE OF CORRECTION

| | |
|---|---|
| PATENT NO. | : 7,358,070 B2 |
| APPLICATION NO. | : 11/062816 |
| DATED | : April 15, 2008 |
| INVENTOR(S) | : Shinya Kozaki et al. |

It is certified that error appears in the above-identified patent and that said Letters Patent is hereby corrected as shown below:

COLUMN 30:

Line 2, "3-hydroxyphenylveleric" should read --3-hydroxyphenylvaleric--;
Line 8, "(R)-3-hydorxypimelyl" should read --(R)-3-hydroxypimelyl--;
Line 10, "bovin" should read --bovine--;
Line 14, "bovin" should read --bovine--;
Line 37, "solution-8" should read --Solution-8--; and
Line 51, "3-hydorx-" should read --3-hydrox--.

COLUMN 31:

Line 1, "bovin" should read --bovine--;
Line 3, "3-hydroxyphenoxylveleric" should read --3-hydroxyphenoxylvaleric--; and
Line 58, "form" should read --from--.

COLUMN 32:

Line 49, "bovin" should read --bovine--.

COLUMN 33:

Line 47, "bovin" should read --bovine--.

COLUMN 35:

Line 10, "bovin" should read --bovine--.

UNITED STATES PATENT AND TRADEMARK OFFICE
CERTIFICATE OF CORRECTION

PATENT NO.        : 7,358,070 B2
APPLICATION NO. : 11/062816
DATED             : April 15, 2008
INVENTOR(S)       : Shinya Kozaki et al.

It is certified that error appears in the above-identified patent and that said Letters Patent is hereby corrected as shown below:

<u>COLUMN 37</u>:

Line 7, "substrate," should read --substrate; and--

Signed and Sealed this

Sixteenth Day of September, 2008

JON W. DUDAS
*Director of the United States Patent and Trademark Office*